(12) United States Patent
Sullivan et al.

(10) Patent No.: US 9,395,340 B2
(45) Date of Patent: Jul. 19, 2016

(54) INTERLEAVED ACOUSTO-OPTICAL DEVICE SCANNING FOR SUPPRESSION OF OPTICAL CROSSTALK

(71) Applicant: KLA-Tencor Corporation, Milpitas, CA (US)

(72) Inventors: Jamie Sullivan, Eugene, OR (US); Wenjian Cai, Sunnyvale, CA (US); Yevgeniy Churin, San Jose, CA (US); Ralph Johnson, Los Gatos, CA (US); Meier Yitzhak Brender, Monte Sereno, CA (US); Mark Shi Wang, San Ramon, CA (US); Rex Runyon, Fremont, CA (US); Kai Cao, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 329 days.

(21) Appl. No.: 13/844,576

(22) Filed: Mar. 15, 2013

(65) Prior Publication Data

US 2014/0260640 A1    Sep. 18, 2014

(51) Int. Cl.
| | |
|---|---|
| G01N 21/88 | (2006.01) |
| G01N 21/95 | (2006.01) |
| G01N 29/24 | (2006.01) |
| G01N 21/956 | (2006.01) |

(52) U.S. Cl.
CPC ........ *G01N 29/2418* (2013.01); *G01N 21/8806* (2013.01); *G01N 21/9501* (2013.01); *G01N 21/956* (2013.01); *G01N 2291/2697* (2013.01)

(58) Field of Classification Search
CPC ............ G01N 21/474; G01N 21/8806; G01N 21/9501; G01N 21/8851; G01N 21/956

USPC ........ 73/655; 356/237.4, 237.5, 237.2, 237.3, 356/73; 359/298; 250/201.3

See application file for complete search history.

(56) References Cited

U.S. PATENT DOCUMENTS

| | | |
|---|---|---|
| 4,391,524 A | 7/1983 | Steigmeier et al. |
| 4,441,124 A | 4/1984 | Heebner et al. |
| 4,614,427 A | 9/1986 | Koizumi et al. |
| 4,889,998 A | 12/1989 | Hayano et al. |
| 4,912,487 A | 3/1990 | Porter et al. |
| 5,317,380 A | 5/1994 | Allemand |
| 5,748,223 A * | 5/1998 | Ito .................................. 347/241 |

(Continued)

OTHER PUBLICATIONS

International Search Report and Written Opinion dated Jul. 28, 2014 for PCT/US2014/025136, filed Mar. 13, 2014 in the name of KLA-Tencor Corporation.

*Primary Examiner* — Helen Kwok
(74) *Attorney, Agent, or Firm* — Bever, Hoffman and Harms, LLP

(57) ABSTRACT

A method of scanning a sample includes simultaneously forming a plurality of co-linear scans. Each scan is formed by a sweep of a spot by an acousto-optical device (AOD). The co-linear scans are separated by a predetermined spacing. A first plurality of swaths are formed by repeating the simultaneous forming of the plurality of co-linear scans in a direction perpendicular to the co-linear scans. The first plurality of swaths have an inter-swath spacing that is the same as the predetermined spacing. A second plurality of swaths can be formed adjacent to the first plurality of swaths. Forming the second plurality of swaths can be performed in an opposite direction to that of the first plurality of swaths or in a same direction. An inspection system can implement this method by including a diffractive optical element (DOE) path after a magnification changer.

26 Claims, 22 Drawing Sheets

(56) References Cited

U.S. PATENT DOCUMENTS

| | | | |
|---|---|---|---|
| 6,208,411 B1 * | 3/2001 | Vaez-Iravani | 356/237.2 |
| 6,236,454 B1 * | 5/2001 | Almogy | 356/237.3 |
| 6,248,988 B1 * | 6/2001 | Krantz | 250/201.3 |
| 6,636,301 B1 * | 10/2003 | Kvamme et al. | 356/237.2 |
| 6,671,042 B1 * | 12/2003 | Almogy | 356/237.3 |
| 6,775,051 B2 | 8/2004 | Sullivan et al. | |
| 6,879,390 B1 * | 4/2005 | Kvamme et al. | 356/237.2 |
| 7,049,155 B2 * | 5/2006 | Reinhorn | 438/7 |
| 7,130,039 B2 * | 10/2006 | Vaez-Iravani et al. | 356/237.5 |
| 7,164,515 B2 * | 1/2007 | Ito et al. | 359/204.1 |
| 2003/0210392 A1 * | 11/2003 | Vaez-Iravani et al. | 356/237.2 |
| 2004/0061042 A1 | 4/2004 | Almogy et al. | |
| 2004/0080740 A1 | 4/2004 | Feldman et al. | |
| 2005/0174570 A1 | 8/2005 | Kvamme et al. | |
| 2006/0197946 A1 * | 9/2006 | Biellak et al. | 356/237.4 |
| 2007/0188744 A1 | 8/2007 | Leslie et al. | |
| 2009/0225399 A1 * | 9/2009 | Zhao et al. | 359/298 |
| 2010/0328759 A1 | 12/2010 | Kirkby et al. | |

* cited by examiner

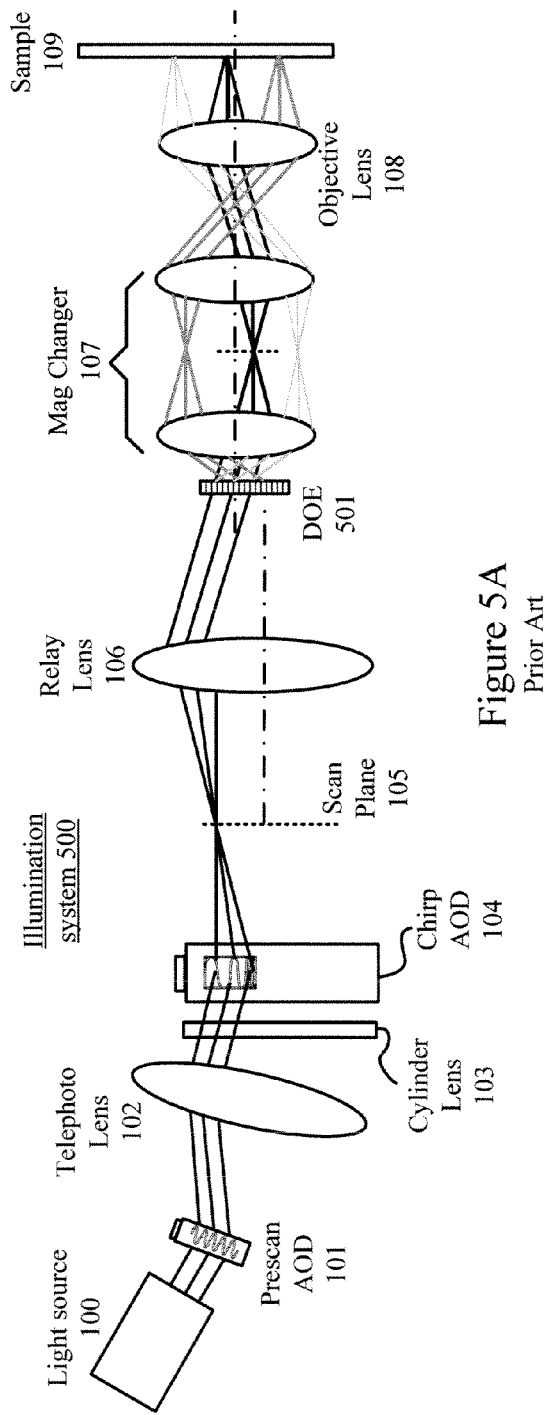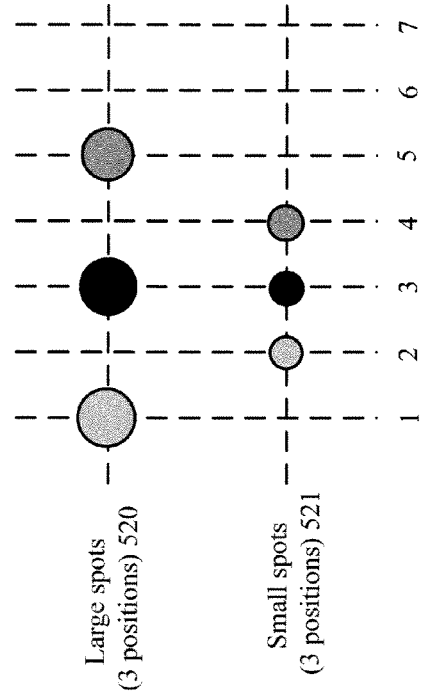
Figure 5A
Prior Art
Figure 5B
Prior Art

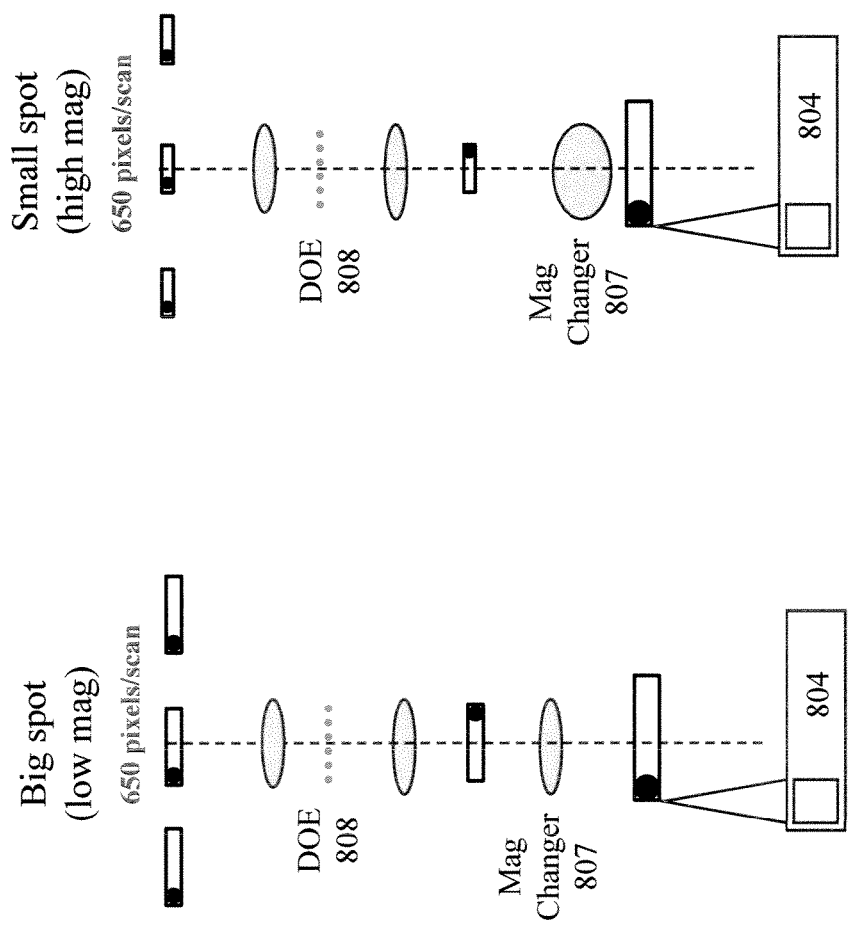

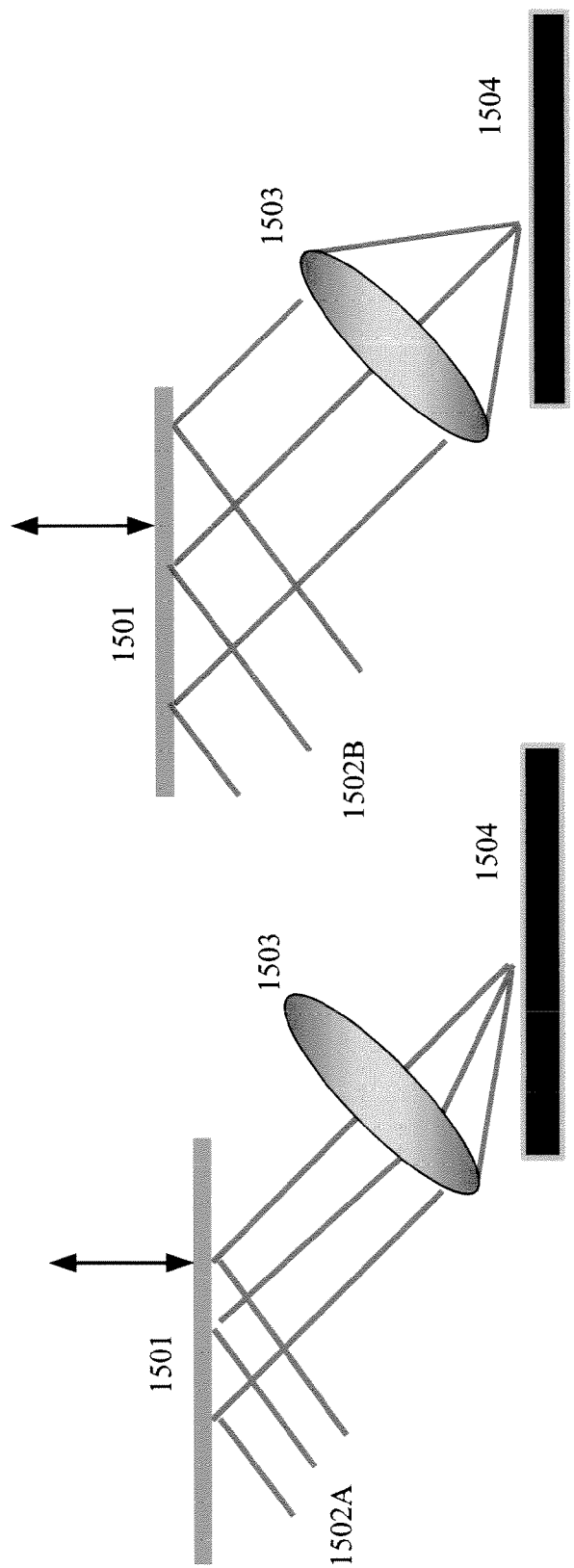

INTERLEAVED ACOUSTO-OPTICAL DEVICE SCANNING FOR SUPPRESSION OF OPTICAL CROSSTALK

BACKGROUND OF THE SPECIFICATION

1. Field of the Invention

Acousto-optical device scanning techniques and systems that suppress optical crosstalk are described.

2. Related Art

During semiconductor fabrication, isolated and/or systemic defects may be formed on the wafer. Isolated defects, which are present in a low percentage of chips on the wafer, may be caused by random events such as an increase in particulate contamination in a manufacturing environment or an increase in contamination in the process chemicals used in the fabrication of the chips. Systemic defects, which are typically present in a high percentage of chips on the wafer, may be caused by defects on a reticle. A reticle is used to transfer a pattern for an integrated circuit layer onto the wafer using photolithographic techniques. Therefore, any defect on the reticle may be transferred with the pattern to each chip of the wafer.

Automated inspection systems have been developed to inspect a wafer surface (both unpatterned and patterned). An inspection system typically includes an illumination system and a detection system. The illumination system may include a light source (e.g. a laser) for generating a beam of light and an apparatus for focusing and scanning the beam of light. Defects present on the wafer surface may scatter the incident light provided by the illumination system (also called an illuminator). The detection system is configured to detect the scattered light and convert the detected light into electrical signals that can be measured, counted, and displayed. The detected signals may be analyzed by a computer program to locate and identify defects on the wafer. Exemplary inspection systems are described in U.S. Pat. No. 4,391,524, issued to Steigmeier et al. on Jul. 5, 1983, U.S. Pat. No. 4,441,124, issued to Heebner et al. on Apr. 3, 1984, U.S. Pat. No. 4,614,427, issued to Koizumi et al. on Sep. 30, 1986), U.S. Pat. No. 4,889,998, issued to Hayano et al. on Dec. 26, 1989, and U.S. Pat. No. 5,317,380, issued to Allemand on May 31, 1994, all of which are incorporated by reference herein.

One or more components used in a state-of-the-art illumination system may use acousto-optics. For example, FIG. 1A illustrates a simplified configuration of an acousto-optical device (AOD) 100. AOD 100 includes a sound transducer 121, a quartz plate 122, and an acoustic absorber 123. An oscillating electric signal can drive sound transducer 121 and causes it to vibrate. In turn, this vibration creates sound waves in quartz plate 122. Acoustic absorber 123 is configured to absorb any sound waves that reach the edge of quartz plate 122. As a result of the sound waves, incoming light 124 to quartz plate 122 is diffracted into a plurality of directions 128, 129 and 130.

A diffracted beam emerges from quartz plate 122 at an angle that depends on the wavelength of the light relative to the wavelength of the sound. By ramping frequencies from high to low, portion 126 may have a higher frequency than portion 127. Because portion 126 has a higher frequency, it diffracts a portion of the incident light beam through a steeper angle as shown by diffracted beam 128. Because portion 127 has a relatively lower frequency, it diffracts a portion of the incident light beam through a more shallow angle as shown by diffracted light beam 130. Because a mid-section portion between portions 126 and 127 has a frequency between the higher and relatively lower frequencies, it diffracts a portion of the incident light beam through an intermediate angle as shown by diffracted light beam 129. This is an example of how an AOD can be used to focus an incoming beam 124 at position 125.

Notably, AODs can operate significantly faster than mechanical devices, such as mirrors. Specifically, AODs can diffract incoming light in approximately the time it takes the sound wave to cross the incoming light beam (e.g. 5-100 ns). Thus, a scan of a sample, e.g. of a wafer or reticle, can be performed at a rate of, for example, 6.32 mm/μsec.

FIG. 1B illustrates an exemplary dual AOD illumination system 110 configured to generate and scan a beam across a sample 109, such as a wafer. A prescan AOD 101 is used to deflect the incident light from a light source 100 at an angle, wherein the angle is proportional to the frequency of the radio frequency (RF) drive source. A telephoto lens 102 is used to convert the angular scan from prescan AOD 101 into a linear scan.

A chirp AOD 104 is used to focus the incident beam in the plane of acoustic propagation onto a scan plane 105. This is accomplished by ramping thru all the RF frequencies with transducer 104A faster than those frequencies can all propagate thru chirp AOD 104. This rapid ramping forms a chirp packet 104B. Chirp packet 104B then propagates thru chirp AOD 104 at the speed of sound. FIG. 1B shows the location of chirp packet 104B at the start of a spot sweep, whereas FIG. 1C illustrates the location of chip packet 104B at the end of that spot sweep. Note that during this propagation, prescan AOD 101 adjusts its RF frequency to track the chirp packet in AOD 104 to keep the light beam incident upon chirp packet 104B.

A cylinder lens 103 is used to focus the beam in a plane perpendicular to the plane of acoustic propagation. A relay lens 106 is used to generate a real pupil at a pupil plane 106A. A magnification changer 107 is used to adjust the size of the spot and the length of sweep. An objective lens 108 is used to focus the spot onto a sample 109, such as a wafer.

FIG. 2 illustrates another exemplary illumination system 200 using a single AOD. In system 200, the prescan AOD is replaced by a beam expander 201. Therefore, this type of illumination system is called a "flood AOD" system. In this configuration, multiple chirp packets 203A and 203B are generated in AOD 104. Note that components having the same numerical references herein are substantially similar components and therefore their descriptions are not repeated. Each chirp packet 203A and 203B generates its own spot. Therefore, objective lens 108 focuses two spots onto sample 109 simultaneously. Although two chip packets are shown in FIG. 2, in other embodiments, additional chirp packets may be generated with a corresponding number of spots incident on sample 109.

Note that sample 109 is typically placed on an XY translation stage capable of bi-directional movement. In this configuration, the stage can be moved so that the focused spots (formed by the focusing optics using the diffracted light beams) impinging sample 109 can be scanned along adjacent contiguous strips of equal width (i.e. raster scan lines). U.S. Pat. No. 4,912,487, issued to Porter et al. on Mar. 27, 1990, and incorporated by reference herein, describes exemplary illumination systems including a translation stage configured to provide raster scanning.

FIG. 3 illustrates a known exemplary AOD scanning technique providing isolation of scattered light for multiple spots. In this embodiment, four spots are scanned during four times 301, 302, 303, and 304 (each spot having a same fill pattern for ease of reference in FIG. 3). These four spots can be generated by an illumination system including an AOD. In FIG. 3, the AOD provides a chirp packet spacing 306 (which also correlates to the spot spacing and the scan line segment length).

FIG. 4 illustrates an exemplary inspection system 400 for the technique described in FIG. 3. In system 400, an AOD optical path, e.g. similar to that shown in FIG. 2, can include an objective lens 404 for focusing the spots generated by the AOD onto a sample 401. System 400 further includes a 50/50 beam splitter (or other ratio) 405 that can direct two copies of the scattered light 402 from the scanned spots on sample 401 to two detector arrays 408 and 409. A first collection path and mask set 406 can be configured to isolate the scattered light from a first set of spots and provide its output to detector array 408, whereas a second collection path and mask set 407 can be configured to isolate the scattered light from a second set of spots and provide its output to detector array 408. Note that each mask has a set of windows, each window having a predetermined width for a given PMT (photomultiplier tube) or other sensor.

Referring back to FIG. 3, the first set of spots is indicated by the boxes having solid lines, whereas a second set of spots is indicated by the boxes having dotted lines. The length of the boxes corresponds to a window width 305 used for the masks in FIG. 4. Thus, for example, at time 301, the scattered light from spots 310 and 312 (using collection path and mask set 406) can be isolated from spot 311 (using collection path and mask set 407). To ensure complete coverage, a mask overlap 307 is provided.

In the scanning technique of FIG. 3, two requirements must be met. First, PMT window width 305 must be smaller than the desired line segment length, which is the spacing of the AOD chirp packet as shown by 306. Second, the PMT windows must overlap, as shown by overlap 307, but must not extend beyond the desired segment length. This requirement ensures that only one spot is within a given mask at any time. Assuming both requirements are met, the scanning technique of FIG. 3 can provide appropriate isolation for the scattered light because at no time are there two spots in a single box.

However, this mask overlap can sometimes result in both arrays of detectors capturing the scattered light from the same spot, as shown by spot 313 at time 301. A similar condition occurs during time 304 for spot 314. This duplicated information must be recognized and accounted for during analysis, thereby increasing collection system complexity. Note also that sometimes a spot is not within the area designated for a mask, as shown by area 315 for time 302 and area 316 for time 303. In those cases, information must still be captured even though no spot is present, thereby wasting resources.

Moreover, 50/50 beam splitter 405 undesirably reduces the light available for detection by one-half. To overcome this disadvantage, a laser (light source) that is 2× higher power would be needed, thereby increasing the cost of the inspection system. Assuming the maximum power laser is already being used, an inspection system using a 50/50 beam splitter would require a large laser. Having multiple chirp packets in the AOD simultaneously as shown in FIG. 2 would have high spot-to-spot crosstalk because of the relatively close proximity of the spots to one another. Moreover, because the PMT window is smaller than the desired line segment length more PMTs are needed, thereby yet further increasing inspection system cost.

FIG. 5A illustrates another exemplary AOD illumination system 500 that can generate multiple spots without flood illumination. In this embodiment, a diffractive optical element (DOE) 501 can be positioned before magnifier changer 107 to generate a plurality of spots. Although FIG. 5A shows three spots being generated (different line colors indicating different beams associated with those spots), other embodiments can generate a different number of spots. FIG. 5B illustrates the effects of changing the magnification of magnifier changer 107 on the spot size, spot spacing, and scan length on sample 109 for illumination system 500. Note that the different fill colors indicate different spots (and correspond to the different line colors of FIG. 5A). As shown in FIG. 5B, large spots 520 have spacing associated with three positions 1, 3, and 5, whereas small spots 521 have spacing associated with three positions 2, 3, and 4. The large spot in position 1 scans to position 3, the large spot in position 3 scans to position 5, and the large spot in position 5 scans to position 7. In contrast, the small spot in position 2 scans to position 3, the small spot in position 3 scans to position 4, and the small spot in position 4 scans to position 5.

Having a smaller spot size (higher magnification), makes appropriate isolation for the scattered light from the multiple spots more difficult. For example, FIGS. 6A and 6B illustrate exemplary sweeps of three small spots 601, 602, and 603 (corresponding to those shown in FIG. 5B) between times $T_1$ and $T_4$. FIG. 6B represents the scans of spots 601, 602, and 603 as boxes of the same color, wherein the boxes represent the paths of the spots as a result of the propagation through the chirp AOD. FIG. 6B shows that there is an overlap of the co-linear scans of different spots (which would occur for both the big spots and the small spots). This overlap will result in undesirable spot crosstalk.

To provide the appropriate isolation between spots, thereby minimizing crosstalk, additional optics and techniques are required. In one embodiment, shown in FIGS. 7A and 7B, a prism 705 can be used in an illumination system to create the appropriate spacing between the spots. U.S. Pat. No. 7,075,638, issued to Kvamme on Jul. 11, 2006, and incorporated by reference herein, describes such an illumination system. In this system, prism 705 and additional optics, such as a spherical aberration correction lens and a transmitted lens, are positioned such that scattered light from the plurality of spots, e.g. beams associated with spots 701, 702, and 703, on the sample are directed to a specific facet of prism 705, as shown in FIG. 7A. In turn, prism 705 directs each beam to a separate detector. FIG. 7B shows the scan sweeps of spots 701, 702, and 703 during operation of the associated inspection system. Prism 705 (which is part of the collector) takes advantage of an offset shown in FIGS. 7A and 7B (the offset being generated by a grating, which is part of the illumination system) to desirably increase the spot isolation. Thus, referring back to FIG. 6B, turning a grating will result in spots 701, 702, and 703 (and their associated scans) no longer being co-linear along the x-axis (i.e. they will instead form a diagonal line with offset scans in a horizontal plane). Unfortunately, prism 705 is designed for a specific magnification. Therefore, if the magnification is changed, then another prism must be used, thereby adding cost and design complexity to the inspection system.

The accurate detection of defects on a sample surface depends on the correct measurement and analysis of each spot in the scan. Therefore, a need arises for optimizing techniques and systems using AODs that ensure the isolation of these spots, thereby minimizing crosstalk, while minimizing system complexity and cost.

SUMMARY

A method of scanning a sample is described. In this method, a plurality of co-linear scans are simultaneously formed. Each scan is formed by a sweep of a spot by an acousto-optical device (AOD). The co-linear scans are separated by a predetermined spacing. A first plurality of swaths are formed by repeating the simultaneous forming of the plurality of co-linear scans in a direction perpendicular to the co-linear scans. The first plurality of swaths have an inter-swath spacing that is the same as the predetermined spacing.

In one embodiment, the predetermined spacing is a scan length. In another embodiment, the predetermined spacing is an integral number of scan lengths. In yet another embodiment, an AOD parameter can be adjusted to provide an integral number of scan lengths as the predetermined spacing.

The method can further include forming a second plurality of swaths adjacent to the first plurality of swaths. In one embodiment, the second plurality of swaths is adjacent to all of the first plurality of swaths except a bottom half of the first plurality of swaths. Forming the second plurality of swaths can be performed in an opposite direction to that of the first plurality of swaths or in a same direction to that of the first plurality of swaths.

Another method of performing a scan of a sample is described. In this method, a spot size and a first scan length is provided using an adjustable magnification changer, a spot separation is provided by a diffractive optical element (DOE) path, and a second scan length is provided by a programmable acousto-optical device (AOD) based on the first scan length. The scan can be performed using the spot size, the spot separation, and the second scan length.

An inspection system is also described. This inspection system includes first and second AODs, a lens, a magnification changer, a first diffractive optical element (DOE) path, and a moveable platform. The first AOD is configured to receive a light beam from a laser and to direct the light beam at various angles along an angular scan. The lens is configured to convert the angular scan to a linear scan. The second AOD is configured to receive the light beam in the linear scan and to generate a scan, the scan being a sweep of a spot, thereby generating a plurality of co-linear spots. The magnification changer is configured to adjust the magnification of the plurality of co-linear spots, thereby generating an adjusted plurality of co-linear spots. The first DOE path is configured to duplicate the adjusted plurality of co-linear spots, thereby generating a set of co-linear scans having a predetermined spacing there between. The moveable platform system is configured to secure a sample and form a first plurality of swaths by moving in a direction perpendicular to the co-linear scans as the first DOE path generates a plurality of sets of the co-linear scans. This movement forms adjacent sets of the co-linear scans. The first plurality of swaths have an inter-swath spacing equal to the predetermined spacing.

The moving platform system is further configured to step in a direction parallel to the co-linear scans and, with the first DOE path, generate a second plurality of swaths. In one embodiment, the second plurality of swaths are formed adjacent to the first plurality of swaths. In another embodiment, the second plurality of swaths are formed adjacent to the first plurality of swaths except for a bottom half of the first plurality of swaths.

The predetermined spacing may be a scan length, an integral number of scan lengths, or a non-integral number of scan. In one embodiment, the second AOD is programmable to provide an adjustable scan length for the second plurality of swaths.

The second plurality of swaths can be formed in an opposite direction to that of the first plurality of swaths or in a same direction to that of the first plurality of swaths.

The first DOE path is for either normal incidence illumination or oblique incidence illumination. In one embodiment, the inspection system further includes a second DOE path and a switching component configured to direct the plurality of co-linear spots to one of the first DOE path and the second DOE path.

The inspection system can further include an anamorphic waist relay positioned to receive the light beam from the laser and configured to allow making adjustments to two independent axes.

When the laser includes a barium borate laser doubling crystal, the inspection system can further include a beam shaper having a slit. The inspection system can further include a pupil and one or more apodization plates placed in operative relation to the pupil and configured to provide a predetermined transmission profile (e.g. in the x-axis and the y-axis) to the plurality of co-linear spots. In one embodiment, the pupil is decentered with respect to objective lenses of the first DOE path. The inspection system may also include an angle of incidence mirror positioned between the magnification changer and the first DOE path. The angle of incidence mirror can be configured to adjust an angle of incidence to the sample.

BRIEF DESCRIPTION OF THE DRAWINGS

FIG. 5A illustrates another exemplary AOD illumination system that can generate multiple spots without flood illumination.

FIG. 5B illustrates the effects of changing the magnification of the magnifier changer on the spot size, spot spacing, and scan length on a sample for the illumination system shown in FIG. 5A.

FIGS. 10A and 10B illustrate a spot size and scan size comparison for big spots and small spots at various points in an illumination system.

FIGS. 15A and 15B illustrate how the angle of incidence can be changed in an oblique illumination system.

DETAILED DESCRIPTION OF THE DRAWINGS

Figure 8A:
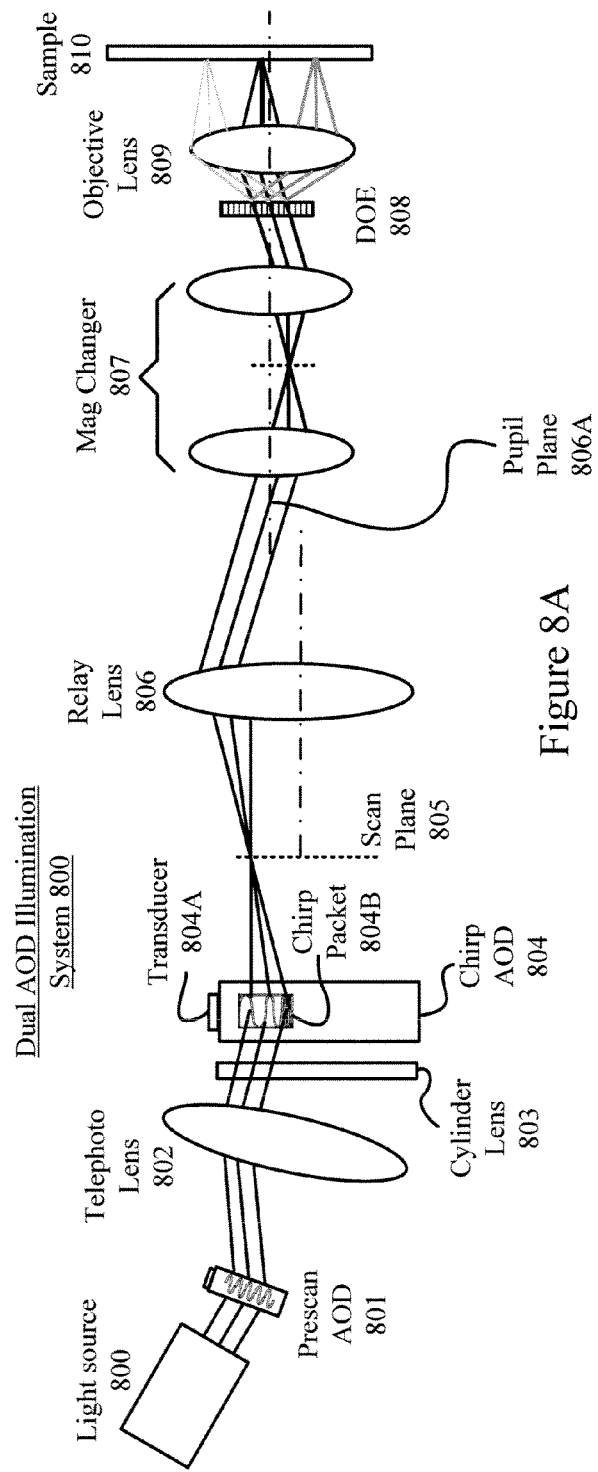
FIG. 8A illustrates an improved dual AOD illumination system configured to generate and scan multiple spots across a sample.

FIG. 8A illustrates an improved dual AOD illumination system 800 configured to generate and scan multiple spots across a sample 810, such as a wafer. A prescan AOD 801 is used to deflect the incident light from a light source 800 at an angle, wherein the angle is proportional to the frequency of the radio frequency (RF) drive source. A telephoto lens 802 is used to convert the angular scan from prescan AOD 801 into a linear scan.

Figure 1A:
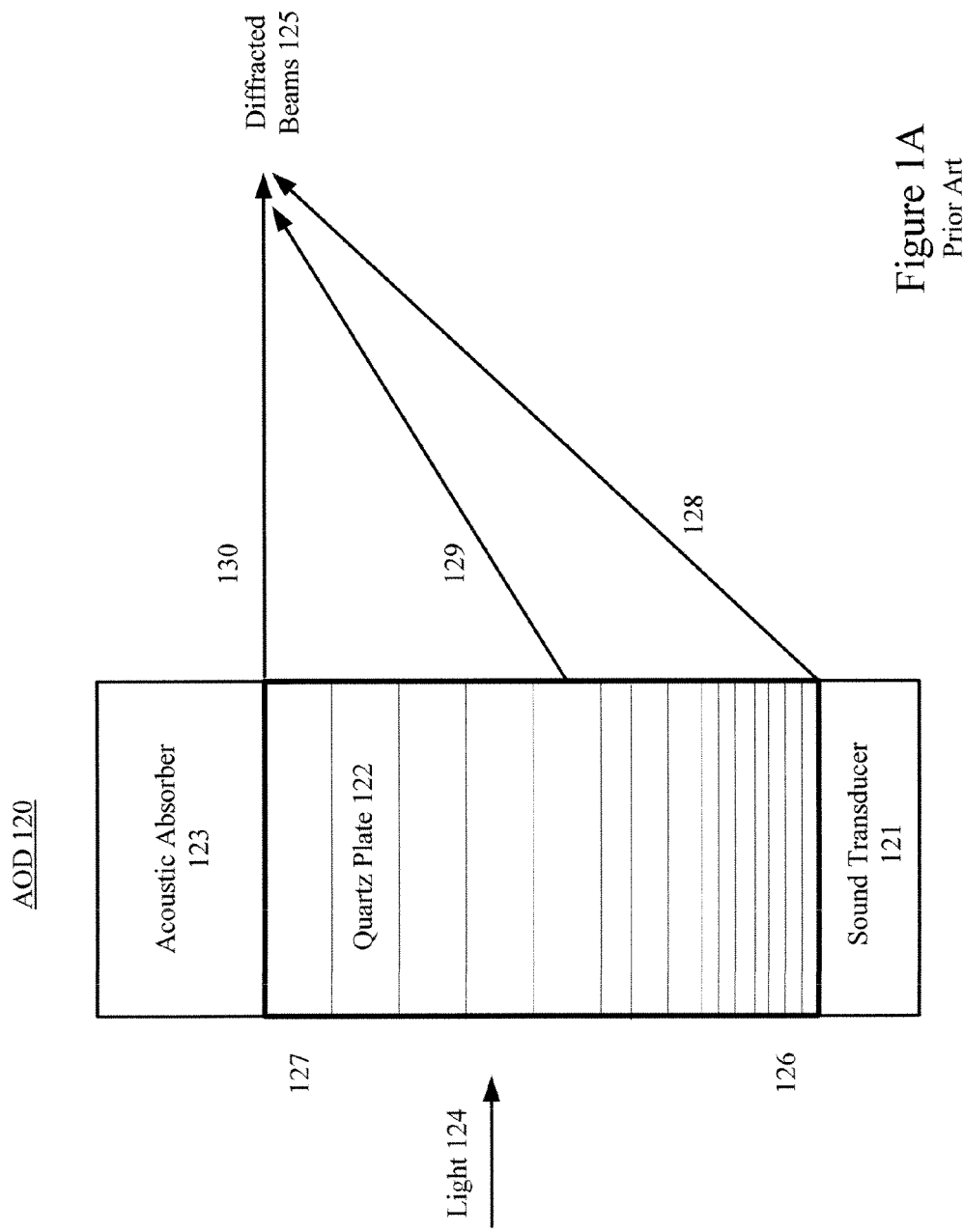
FIG. 1A illustrates a simplified configuration of an acousto-optical device (AOD).
Figure 1B:
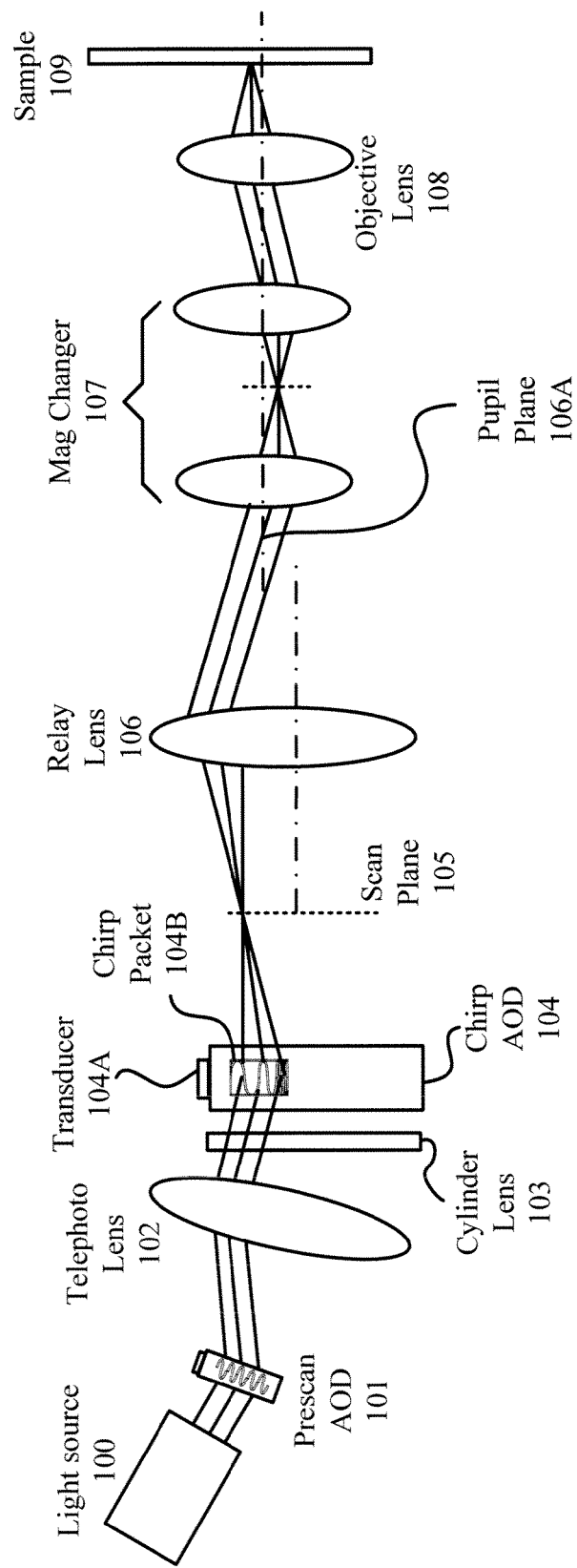
FIG. 1B illustrates an exemplary dual AOD illumination system configured to generate and scan a beam across a sample, such as a wafer.
Figure 1C:
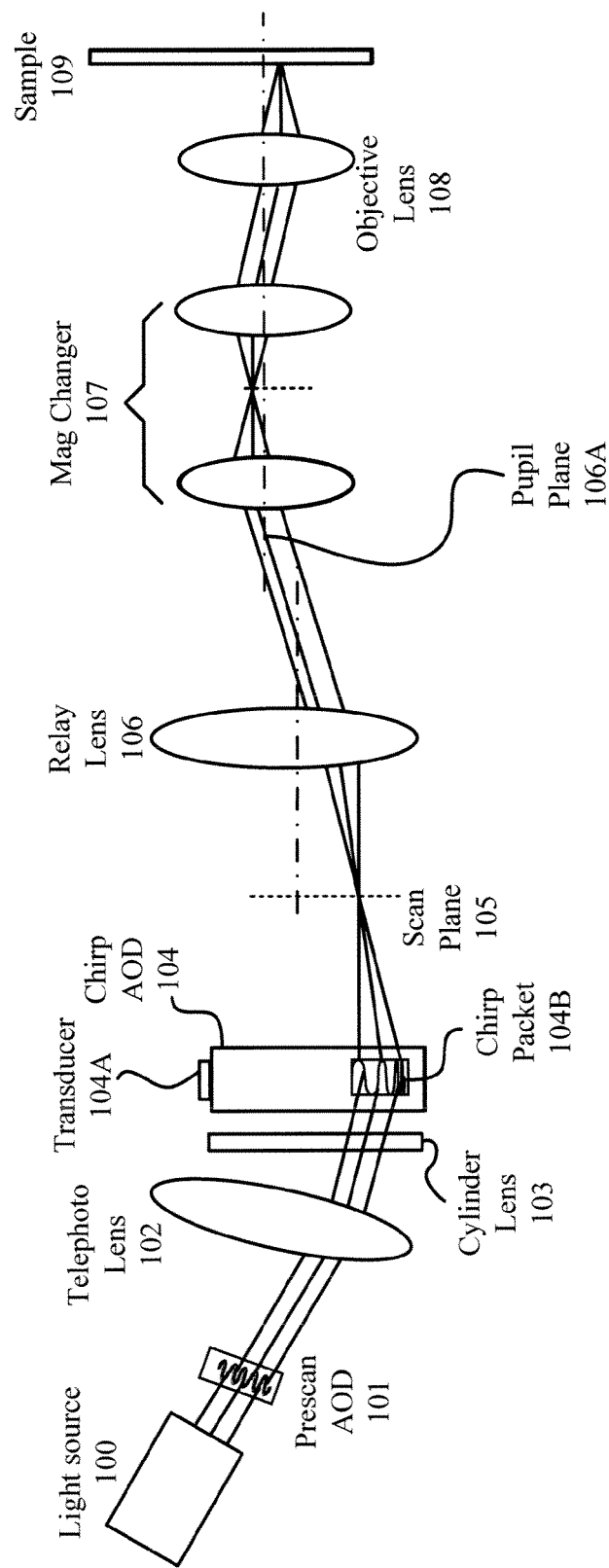
FIG. 1C illustrates the location of a chip packet at the end of a spot sweep of the dual AOD illumination system shown in FIG. 1B.
Figure 2:
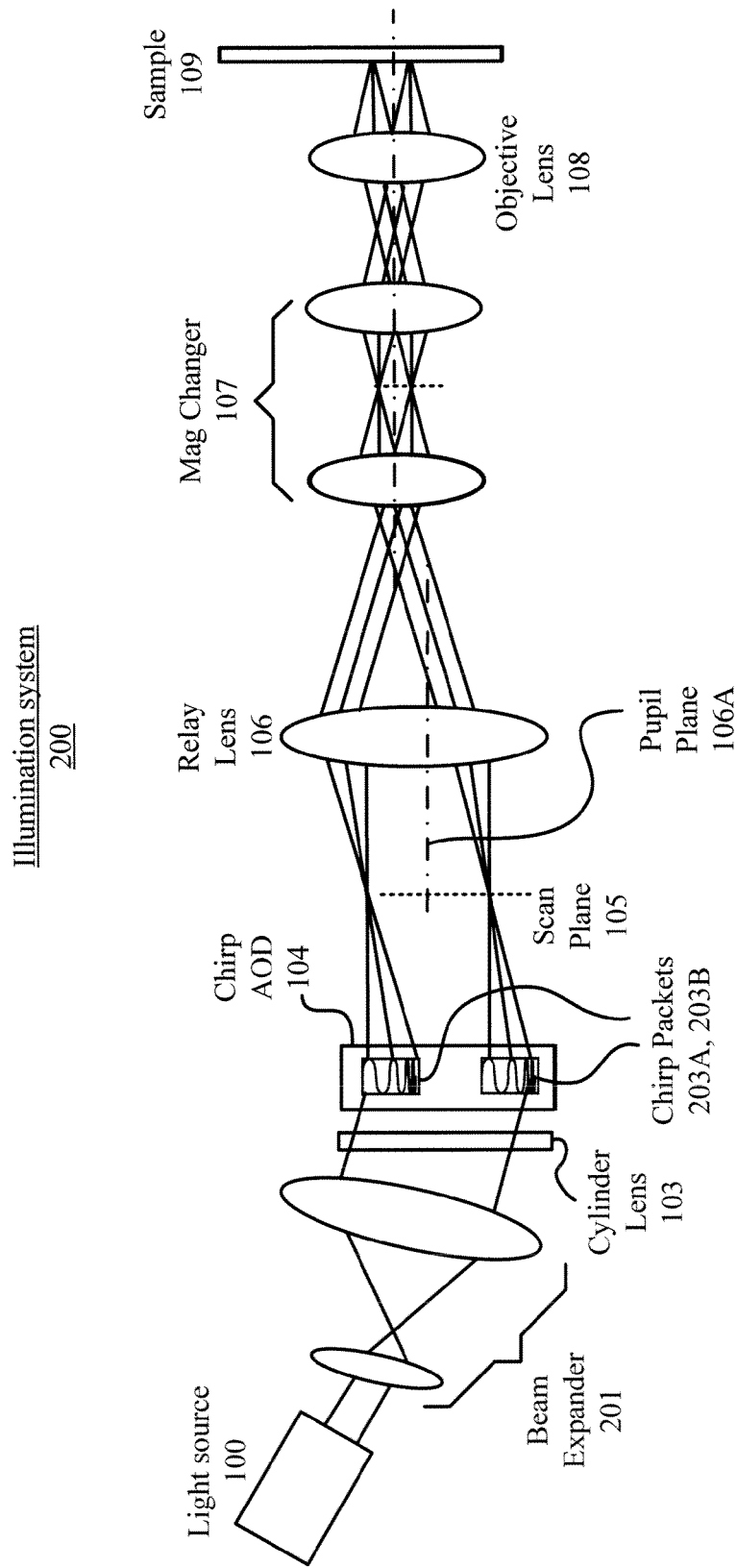
FIG. 2 illustrates another exemplary illumination system using a single AOD.
Figure 3:
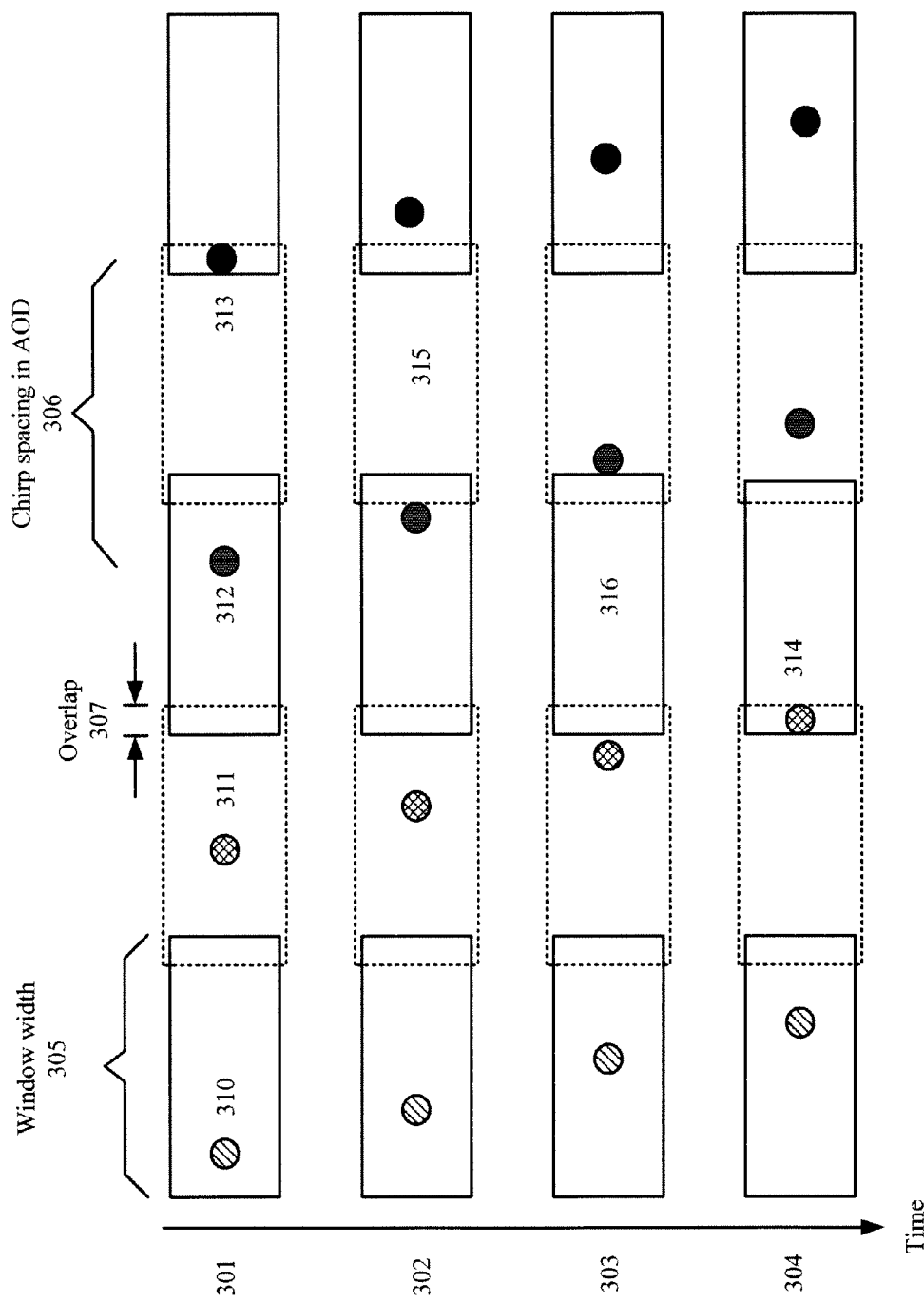
FIG. 3 illustrates a known exemplary AOD scanning technique providing isolation of scattered light for multiple spots.
Figure 4:
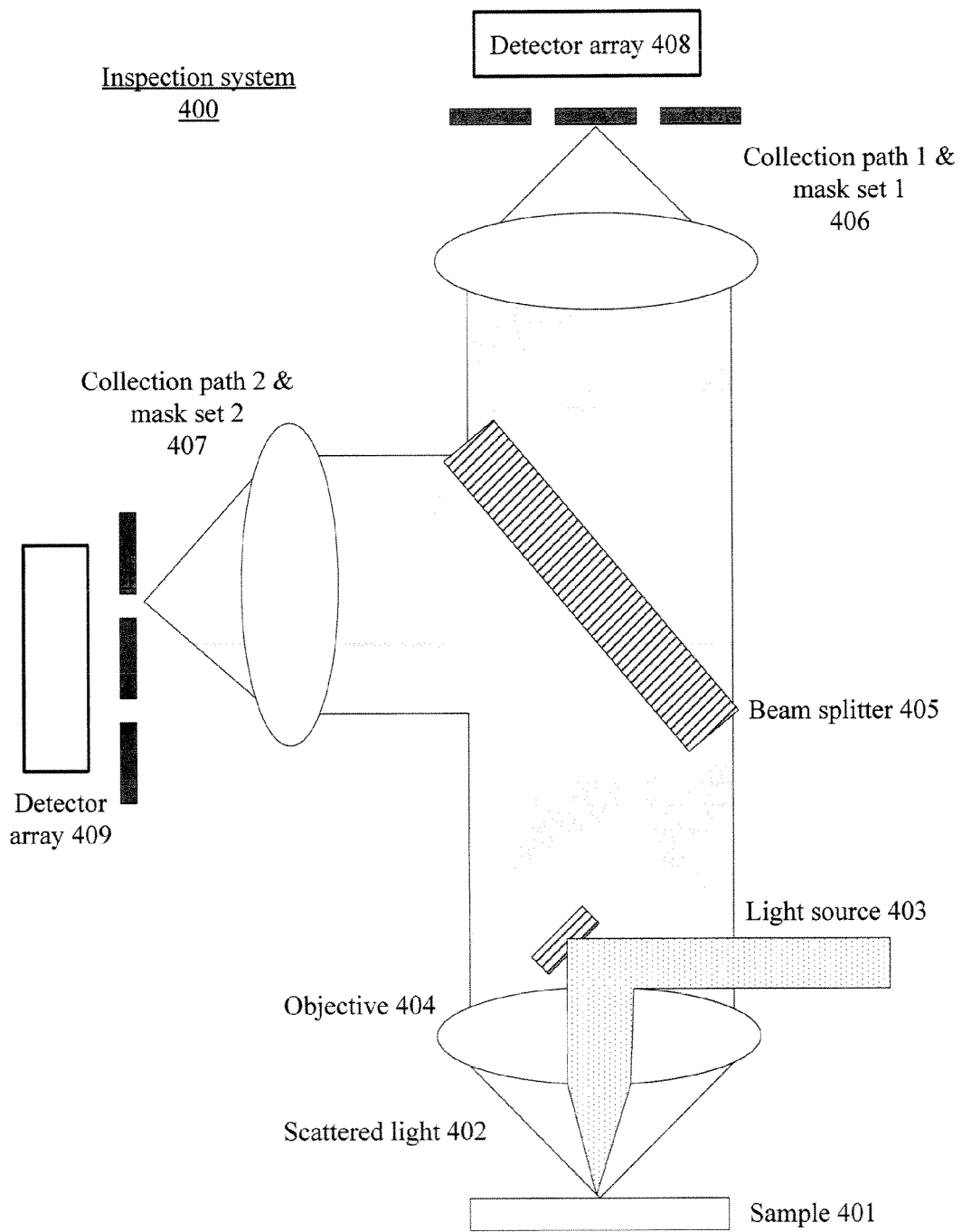
FIG. 4 illustrates an exemplary inspection system for the technique described in FIG. 3.
Figure 6B:
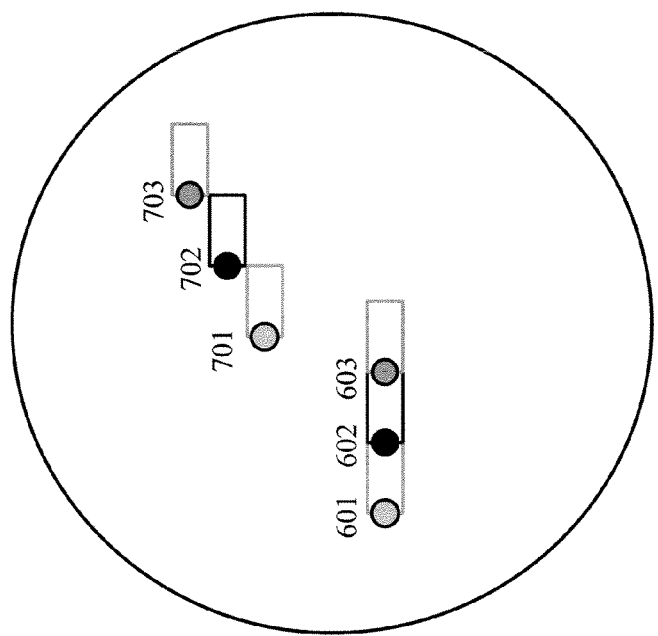
FIGS. 6A and 6B illustrate exemplary sweeps of three small spots.
Figure 6A:
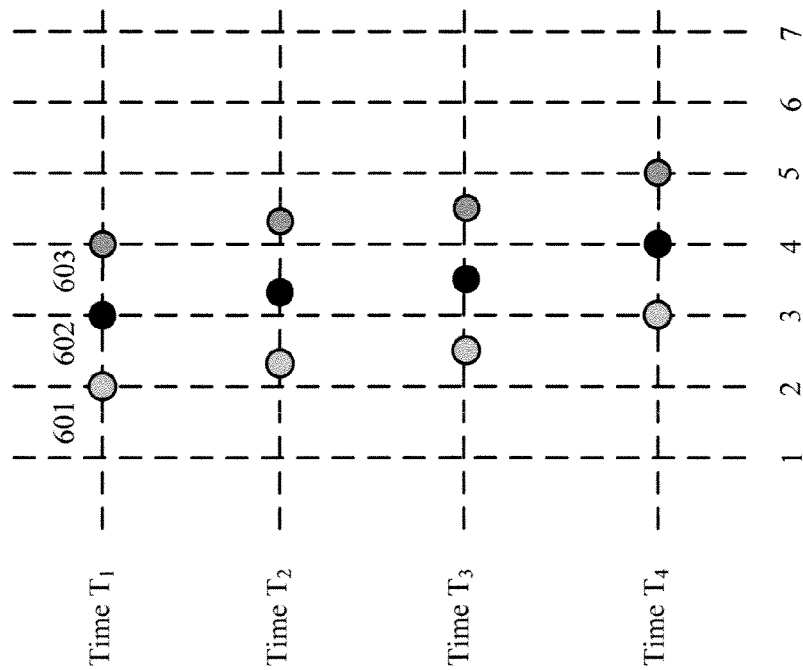
Figure 7B:
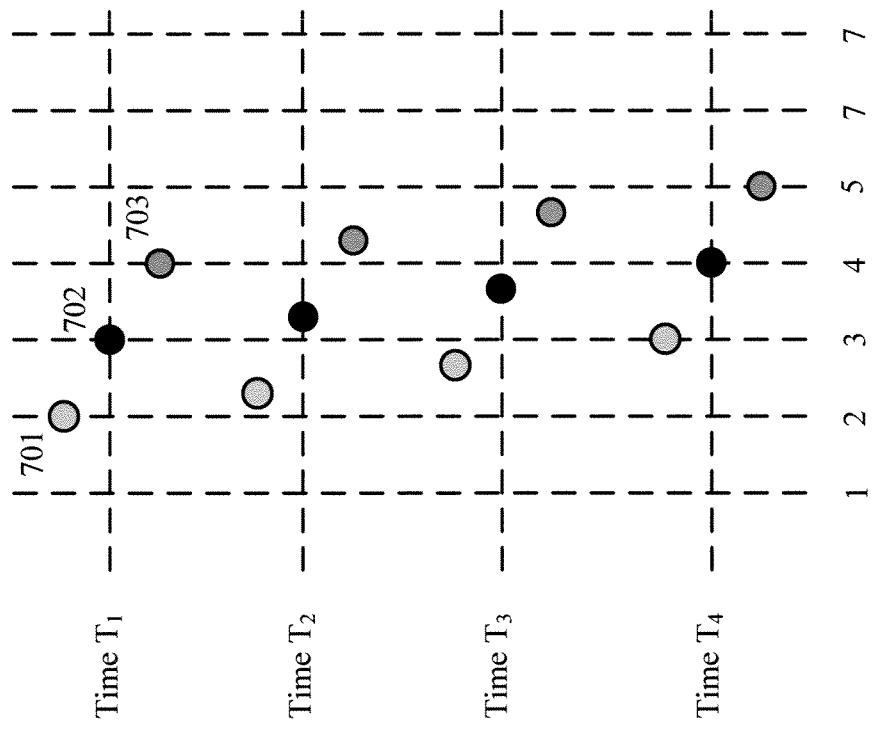
FIGS. 7A and 7B illustrate how a prism can be used in conjunction with an illumination system to create an appropriate isolation of spots in the collector optics.
Figure 7A:
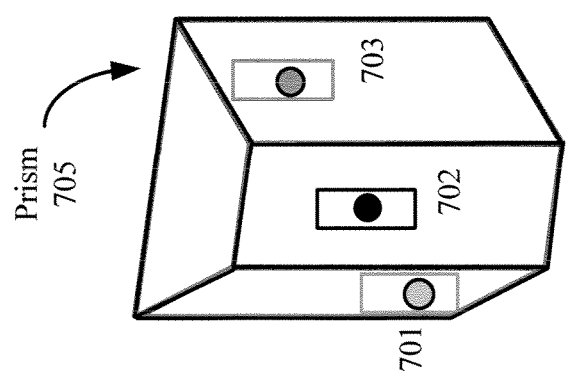

A chirp AOD 804 is used to focus the incident beam in the plane of acoustic propagation onto a scan plane 805. This is accomplished by ramping thru all the RF frequencies with its transducer 804A faster than those frequencies can all propagate thru chirp AOD 804. This rapid ramping forms a chirp packet 804B. Chirp packet 804B then propagates thru chirp AOD 804 at the speed of sound. The location of chirp packet 804B propagates across chirp AOD 804 during the spot sweep (see, e.g. FIGS. 1B and 1C for a similar movement). Note that during this propagation, prescan AOD 801 adjusts its RF frequency to track the chirp packet in AOD 804 to keep the light beam incident upon chirp packet 804B.

A cylinder lens 803 is used to focus the beam in a plane perpendicular to the plane of acoustic propagation. A relay lens 806 is used to generate a real pupil at a pupil plane 806A. A magnification changer 807 is used to adjust the size of the spot and the length of sweep. Notably, a diffractive optical element (DOE) 808 is positioned after magnification changer 807 and before an objective lens 809. DOE 808 makes copies of the spot output by magnification changer 807 without changing the spot spacing, as described below. Although FIG. 8A shows three spots being generated by DOE 808, other embodiments may have a different number of spots. Objective lens 809 is used to simultaneously focus the multiple spots onto sample 810.

Figure 8B:
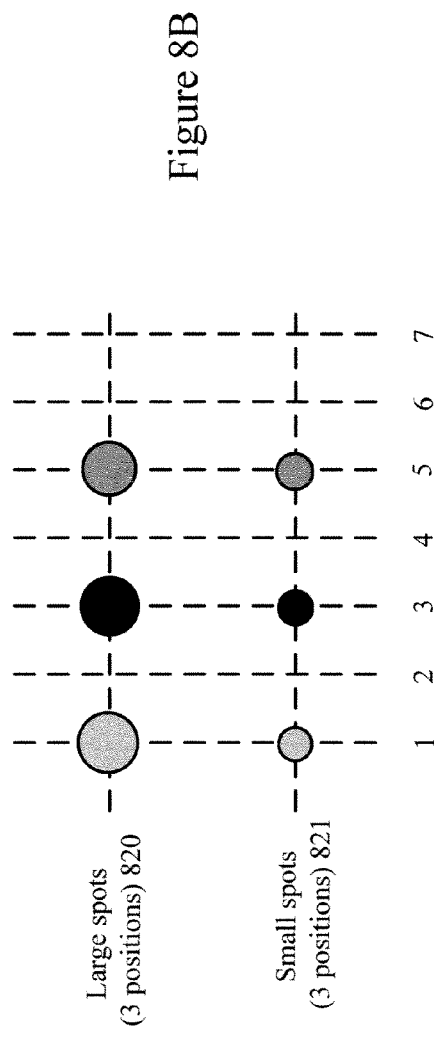
FIG. 8B illustrates the effects of changing the magnification of the magnifier changer on the spot size and spot spacing on the sample for the illumination system shown in FIG. 8A.

FIG. 8B illustrates the effects of changing the magnification of magnifier changer 807 on the spot size and spot spacing on sample 810 for illumination system 800. Note that the different fill colors indicate different spots (and correspond to the different line colors of FIG. 8A). As shown in FIG. 8B, both large spots 820 and small spots 821 can have identical spacing associated with three positions 1, 3, and 5.

Figure 9A:
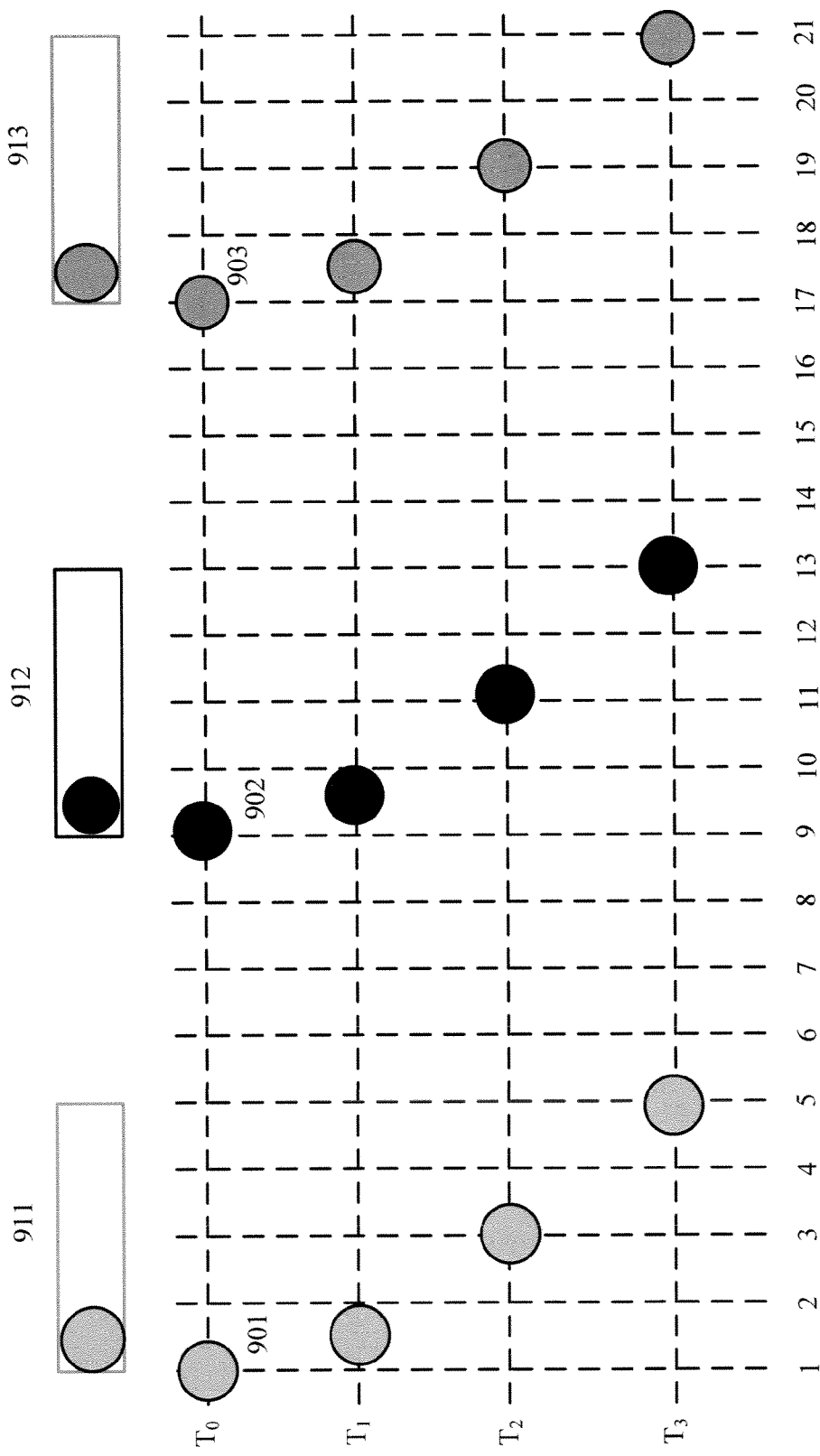
FIGS. 9A and 9B illustrate exemplary scans of three large spots and three small spots generated by the illumination system shown in FIG. 8A.
Figure 9B:
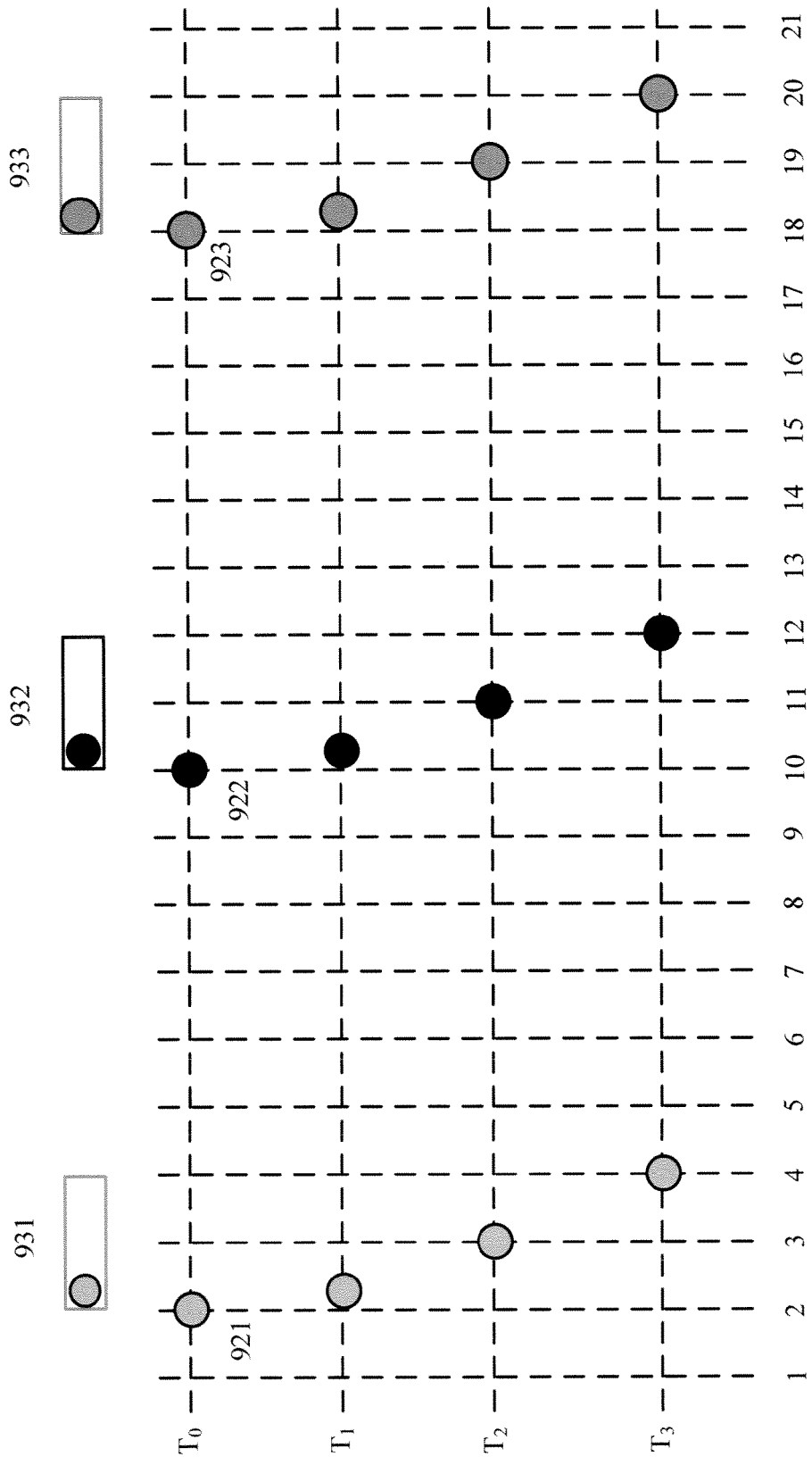
Figure 9C:
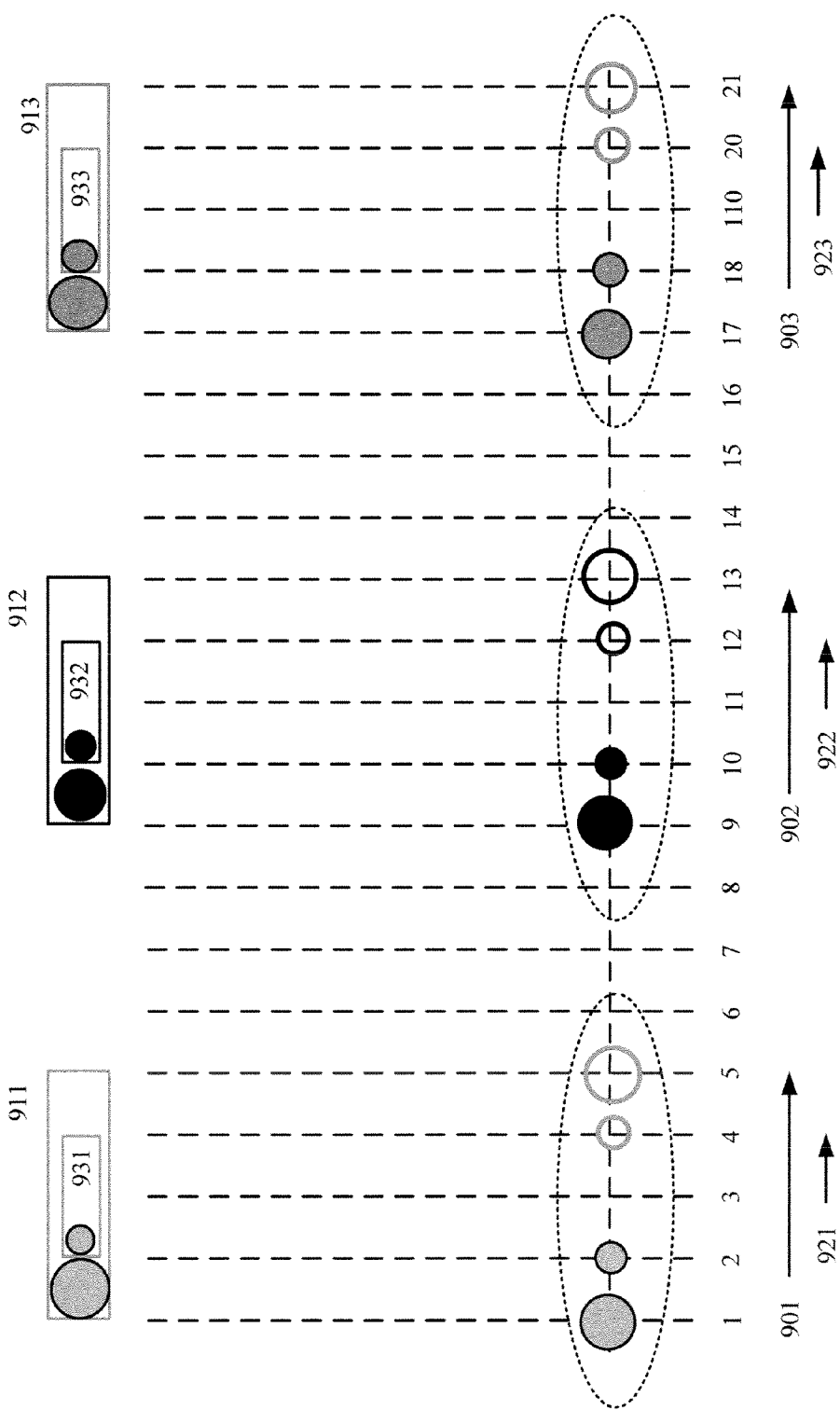
FIG. 9C illustrates the superposition of the scans of the large and small spots shown in FIGS. 9A and 9B.

FIG. 9A illustrates exemplary scans of three large spots 901, 902, and 903 (corresponding to spots 820 shown in FIG. 8B) between times $T_1$ and $T_4$. FIG. 9A represents the sweeps of spots 901, 902, and 903 as boxes 911, 912, and 913, respectively. FIG. 9B illustrates exemplary scans of three small spots 921, 922, and 923 (corresponding to spots 821 shown in FIG. 8B) between times $T_1$ and $T_4$. FIG. 9B represents the scans of spots 921, 922, and 923 as boxes 931, 932, and 933, respectively. FIG. 9C shows that large spot 901 in position 1 scans to position 5, large spot 902 in position 9 scans to position 13, and large spot 903 in position 17 scans to position 21. In contrast, small spot 921 in position 2 scans to position 4, small spot 922 in position 10 scans to position 12, and small spot 923 in position 18 scans to position 20. Therefore, the scans of the three small spots can be "nested" in the scans of the three large spots. That is, scans 931, 932, 933 can be nested in scans 911, 912, and 913, respectively. As shown in FIG. 9C, when the collection optics are designed to collect the light from the low magnification configuration (big spot), they will by default collect the light from the high magnification configuration (small spot).

FIGS. 10A and 10B illustrate a spot size and scan size comparison for big spots and small spots at various points in an illumination system. As shown, chip AOD 804 (see FIG. 8) generates spots having the same spot size and scan size; however, the magnification changer 807 changes both the spot size and scan size. In one embodiment, both big and small spots are reduced in size; however, magnification changer 807 creates a size differential between the big spots and the small spots at this stage. Note that the magnification also changes the image orientation (shown by the spot position switch from one side to another in the scan), which is typical for a magnifier. DOE 808 creates copies of the spots, wherein as noted above, the scan positions between big and small spots is the same, although the spacing between the scans for the big and small spots differs. Specifically, there is a bigger spacing between the small spot scans than for the big spot scans.

Figure 11B:
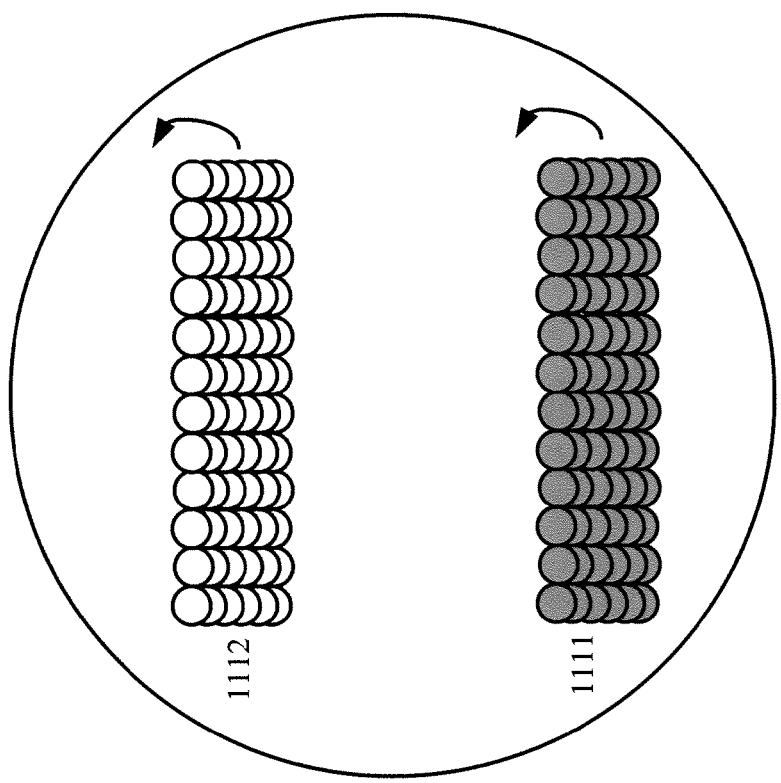
FIGS. 11A-11D illustrate a technique for scanning using the small spots of FIG. 10B.
Figure 11A:
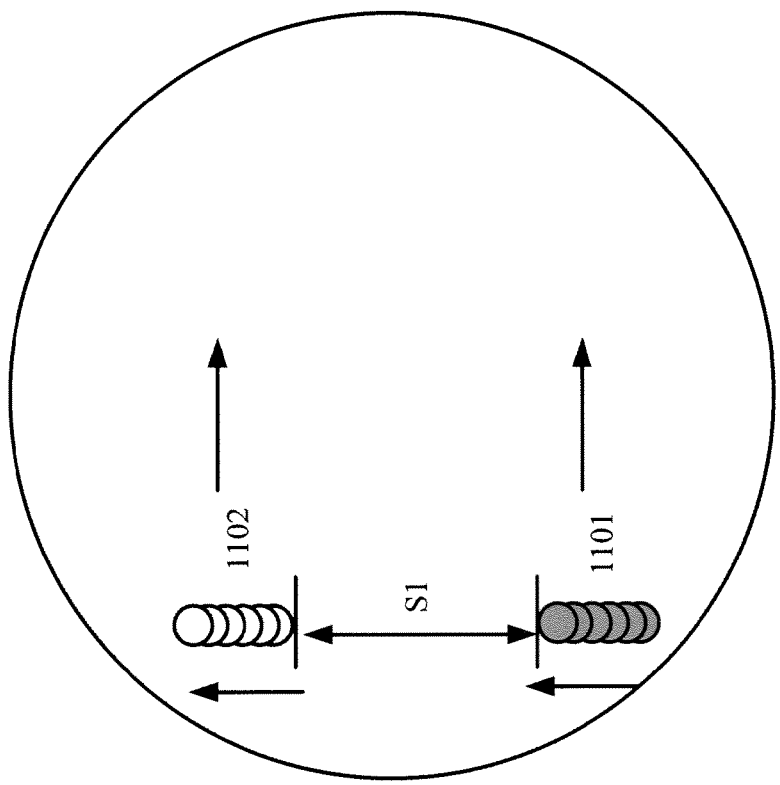
Figure 11D:
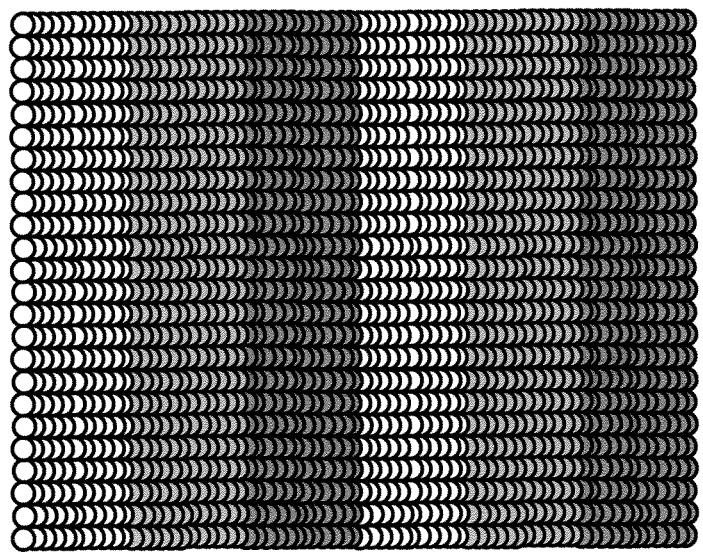
Figure 11C:
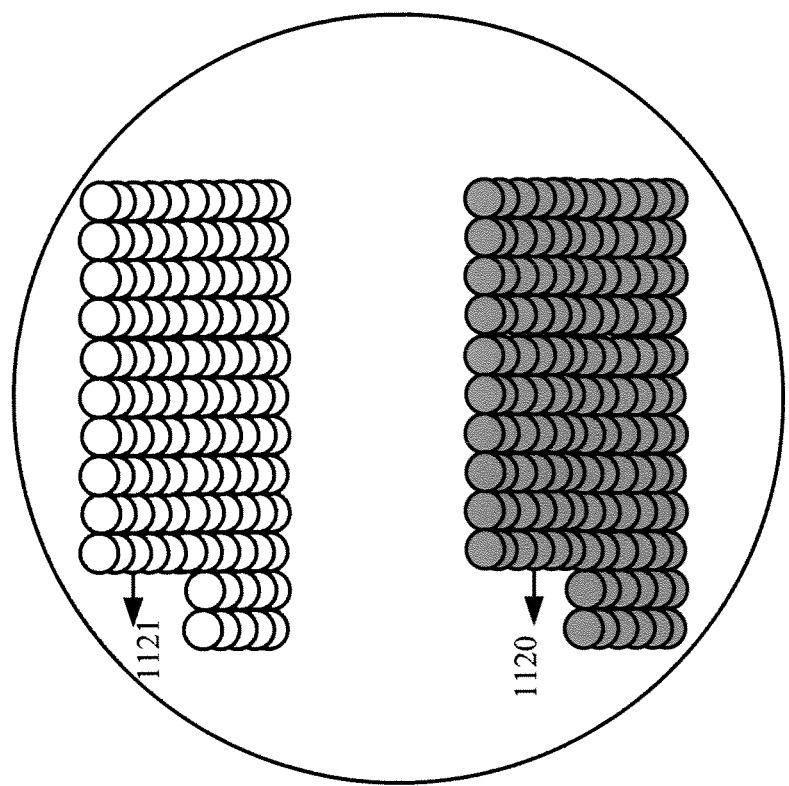

FIGS. 11A-11D illustrate a technique for scanning using the small spots of FIG. 10B. Notably, this technique can be used for both normal incidence illumination as well as oblique incidence illumination. In this embodiment, completed scans (two spots shown for simplicity) form a dashed co-linear line. That is, referring to FIG. 11A, scans 1101 and 1102 (formed bottom to top in this case) have a spacing S1 there between. Therefore, a large spatial separation of the beams is ensured. In one embodiment, the scans are formed vertically (as shown) and the swaths are formed horizontally. For example, referring to FIG. 11B, swaths 1111 and 1112 can be formed by repeating the scans 1101 and 1102, respectively in a left to right movement. After the swaths are formed (with corresponding spaces S there between, also called blanks herein), another set of swaths can be formed in the spaces/blanks in a direction opposite to that used to form the previous sets of swaths. For example, swaths 1120 and 1121 can be formed right to left (shown only as partial swaths for clarity), whereas swaths 1101 and 1102 (see arrows of FIG. 11A, and resulting swaths in FIG. 11B) were formed left to right. In one embodiment, a stage that positions the wafer can be stepped, e.g. by one scanning beam, to form each new scan (i.e. column of spots). After the swath interleaving is complete, additional interleaved swaths can be formed in a similar manner to that described in FIGS. 11A-11C to provide a complete scan of a sample, as shown in FIG. 11D (which assumes a 3-spot DOE).

Note that spacing S1 can be designed to fit an integral number of scans, thereby ensuring a complete scan of the wafer without duplicate information. In one embodiment, this inter-swath spacing can be adjusted using a chirp parameter of a programmable AOD, which is described below in reference to FIG. 14. Because spacing S1 is greater than one scan length, a few small vertical adjustments (e.g. one scan length) can be made to create the necessary fill-in swaths before a large vertical adjustment is made.

Figures 12A, 12B:
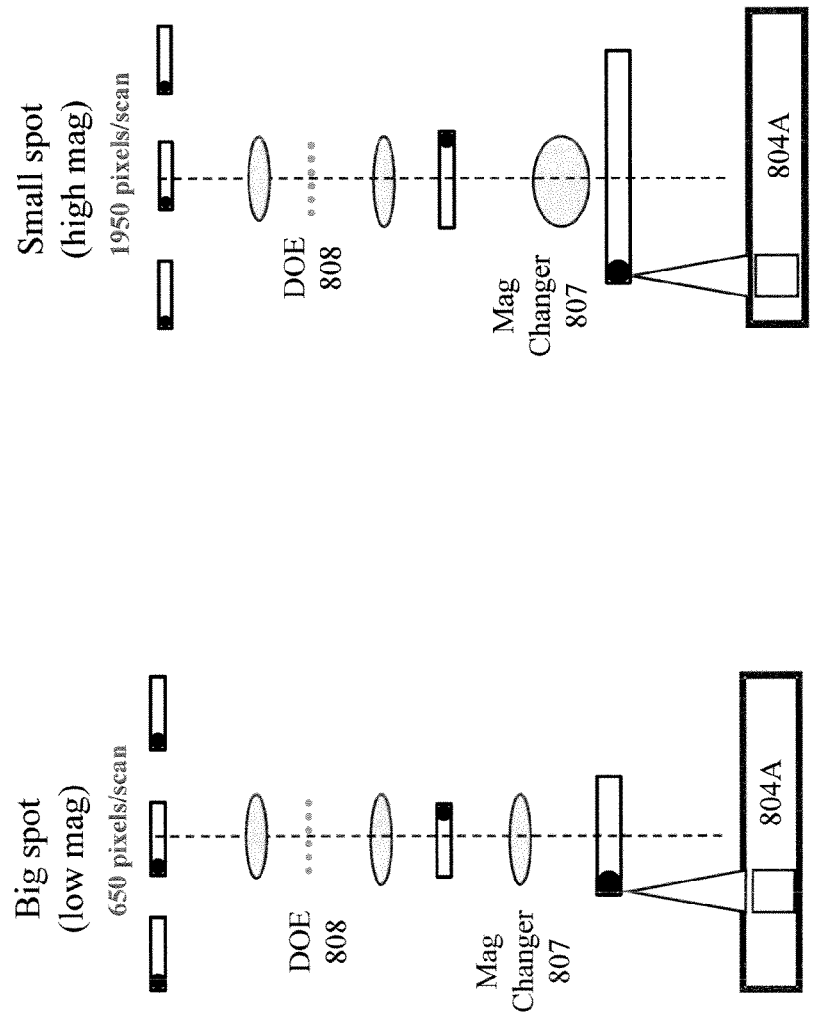
FIGS. 12A, 12B, and 12C illustrate a spot size and scan size comparison for big spots and small spots at various points in another illumination system.
Figure 12C:
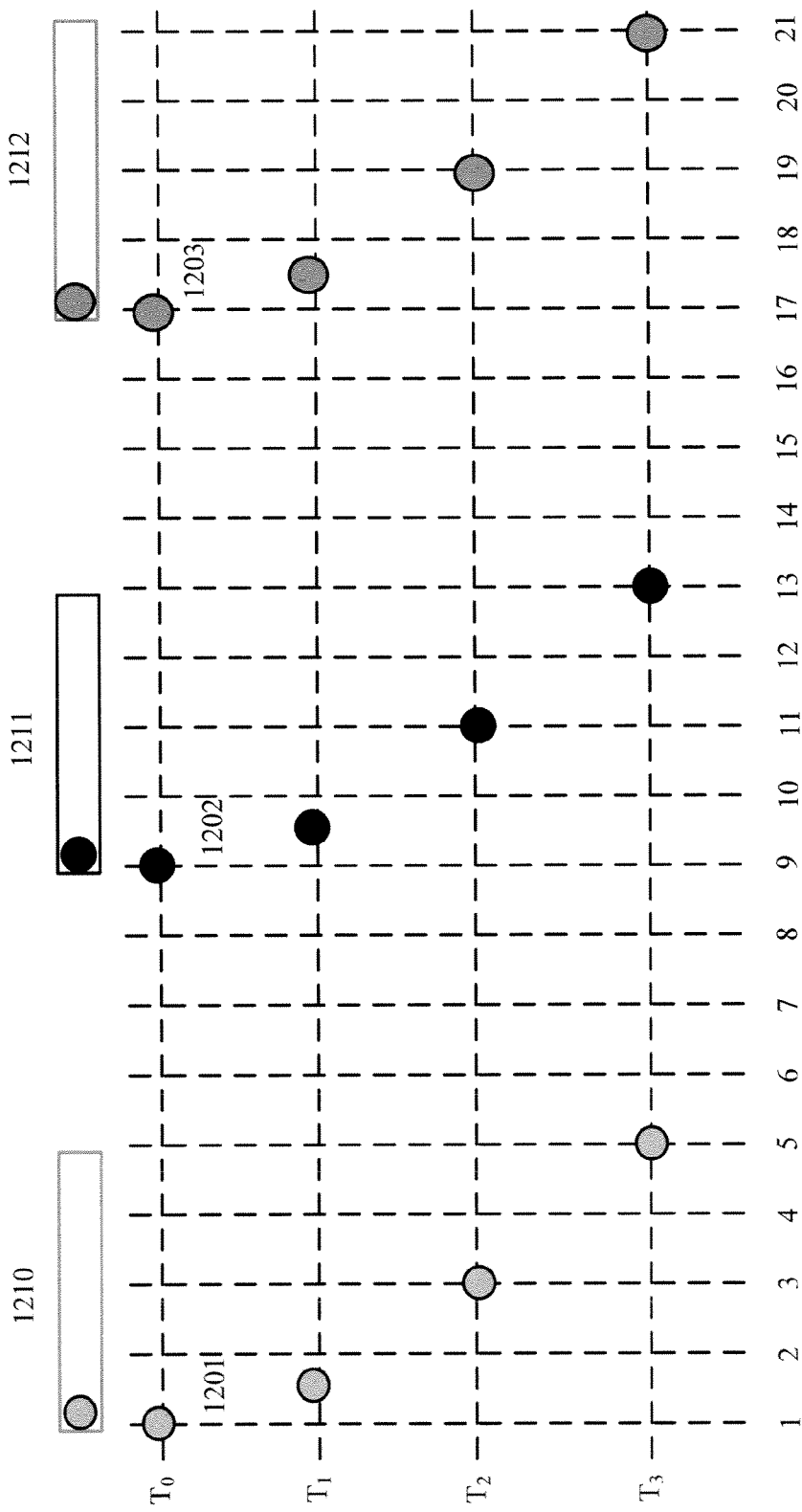
Figure 13B:
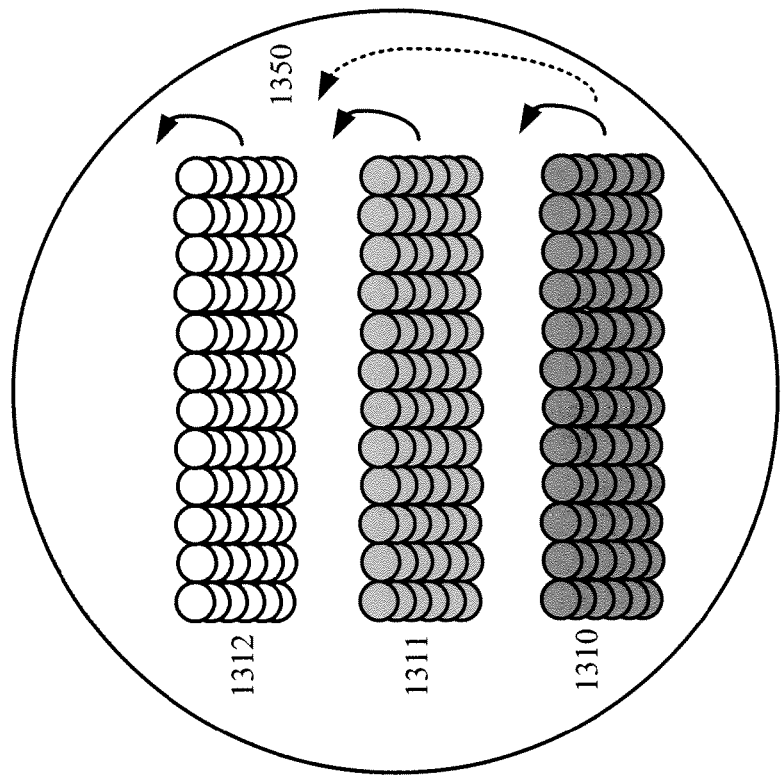
FIGS. 13A-13D illustrate a technique for scanning using the small spots of FIG. 12B.
Figure 13A:
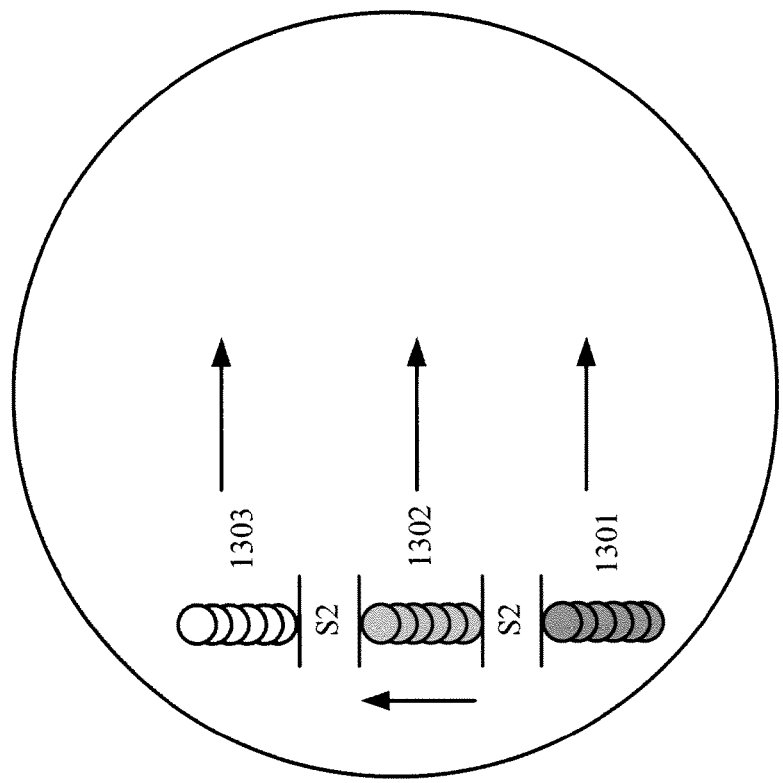
Figure 13D:
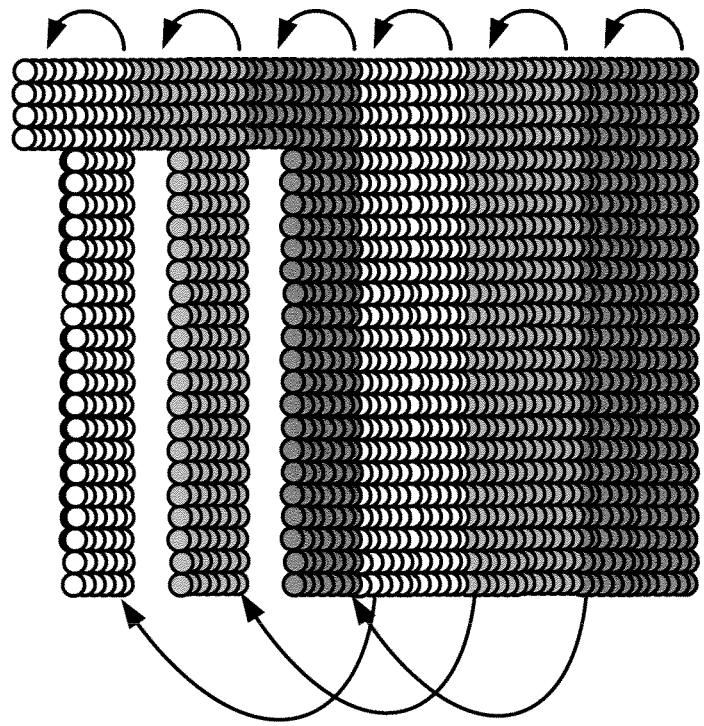
Figure 13C:
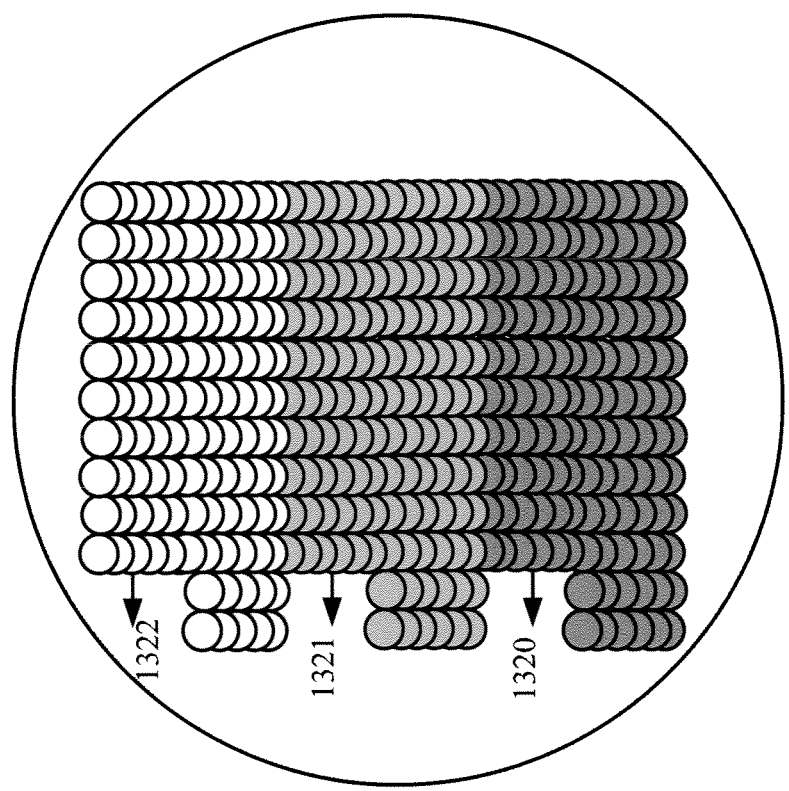

FIGS. 12A and 12B illustrate a spot size and scan size comparison for big spots and small spots at various points in another illumination system. In this embodiment, a programmable AOD 804A with software control can be used. This software control allows a longer scan to be selectively generated, if desired. However, the functioning of magnification changer 807 and DOE 808 is the same as that described above. That is, chip AOD 804 (see FIG. 8) generates spots having the same spot size and scan size; however, the magnification changer 807 changes both the spot size and scan size. DOE 808 creates copies of the spots. Notably, by using programmable AOD 804A, the scan size (but not spot size) can be increased. Therefore, DOE 808 can generate scans with smaller spacing there between. FIG. 12C shows that small spot 1201 in position 1 scans to position 5, small spot 1202 in position 9 scans to position 13, and small spot 1203 in position 17 scans to position 21. Notably, scans 1210 (including spot 1201), 1211 (including spot 1202), and 1212 (including spot 1203) have a spacing there between that permits exactly one scan length. This spacing can be leveraged, as described below.

Note that when comparing FIG. 10B with FIG. 12B, the throughput of an inspection system including the configuration of FIG. 12B will be greater. Specifically, the actual scan rate will be the same. The scan rate is proportional to the size of the scanning spot and the velocity of the scanning spot. In FIGS. 10B and 12b, the size of the spot and the velocity is the same. However, the XY stage will be slower for the configuration of FIG. 12B, i.e. the set-up is necessarily longer because it must still wait for the longer scan to finish. In addition, the height of the swath is larger for FIG. 12B as indicated by the number of pixels per segment shown in FIGS. 10A, 10B, 12A, and 12B, which in this embodiment are all 650 pixels per scan, except for the configuration of FIG. 12B, which is 1950 pixels per scan. Note that when a larger spot size is provided, a correspondingly faster velocity results, and a smaller spot size corresponds to a slower velocity. Thus, it takes the same amount of time for the large spot to travel its scan as the small spot to travel its scan in FIGS. 10A and 10B. However, referring to FIGS. 12A and 12B, because the scan size is bigger (i.e. the scan length is longer), then it takes longer for the small spot to travel its scan compared to the large spot to travel its scan (1950 pixels versus 650 pixels). Throughput is based on how fast a certain area of the wafer can be scanned, which will be determined by the velocity of the scan and the spot size. Starting and stopping the XY stage for forming the swaths is overhead because the spot scanning is not being done during those periods. Therefore, reducing the overhead by reducing the number of swaths and hence the number of times the XY stage must be stopped and started improves the throughput of the inspection system as illustrated by FIG. 12B. Moreover, it also takes time to set up the pre-scan AOD and other various electronics between scans. Thus, even more overhead can be averted by lengthening the scan, e.g. as that shown in FIG. 12B. The peak data rate is always the rate for digitizing the pixels when the spot is moving. Thus, the peak data rate is the same for any of configurations shown in FIGS. 10A, 10B, 12A, and 12B. However, the average data rate (which is always lower than the peak data rate) will vary based on the overhead. Thus, the configuration shown in FIG. 12B provides the fastest average data rate (and closest to the peak data rate) of the configurations shown in FIGS. 10A, 10B, 12A, and 12B.

FIGS. 13A-13D illustrate a technique for scanning using the small spots of FIG. 12B. In this embodiment, completed scans (three spots shown for simplicity) also form a dashed co-linear line with small spaces between scans. That is, referring to FIG. 13A, scans 1301 and 1302 (formed bottom to top in this case) have a spacing S2 there between. Spacing S2 is smaller than spacing S1, however, sufficient spatial separation of the beams using spacing S2 is still ensured. The spacing S1 and spacing S2 are controlled by the length of the scan in the chirp AOD, and are optimized when the spacing is equal to the length of the scan (scan size).

In one embodiment, the scans are formed vertically (as shown) and the swaths are formed horizontally. For example, referring to FIG. 13B, swaths 1310, 1311, and 1312 can be formed by repeating the scans 1301, 1302, and 1303, respectively in a left to right movement. After the swaths are formed (with corresponding spaces S2 there between), another set of swaths can be formed in the spaces/blanks in a direction opposite to that used to form the previous sets of swaths. For example, swaths 1320, 1321, and 1322 can be formed right to left (shown only as partial swaths for clarity), whereas swaths 1310, 1311, and 1312 (see arrows of FIG. 13A, and resulting swaths in FIG. 13B) were formed in a left to right pattern. Once again, a stage that positions the sample can be stepped, e.g. by one scanning beam. After the swath interleaving is complete, additional interleaved swaths can be formed in a similar manner to that described in FIGS. 13A-13C to provide a complete scan of the sample. Because spacing S2 is equal to one scan length, one small vertical adjustment (i.e. one scan length or scanning beams) can be made to create the necessary fill-in swath before a large vertical adjustment is made. In one embodiment, shown in FIG. 13D, the stage can step 5 scanning beams (e.g. 1⅔ of the field of view (FOV)). In another embodiment, and referring to FIG. 13B, instead of moving up one scan length after finishing swaths 1310, 1311, and 1312, the next and all subsequent vertical adjustments could be that shown by arrow 1350. Note that this fill-in pattern depends on the number of spots, e.g. for a 5 spot pattern, 2 blanks are left; for a 7 spot pattern, 3 blanks are left. Thus, in general, a second plurality of swaths are formed adjacent to all of the first plurality of swaths except a bottom half of the first plurality of swaths. This fill-in pattern provides complete coverage with the exception of the space between swaths 1310 and 1311. In this configuration, swath 1311 would then designate the first area of interest on the wafer. This technique can be applied to other configurations that utilize more spots.

Figure 14:
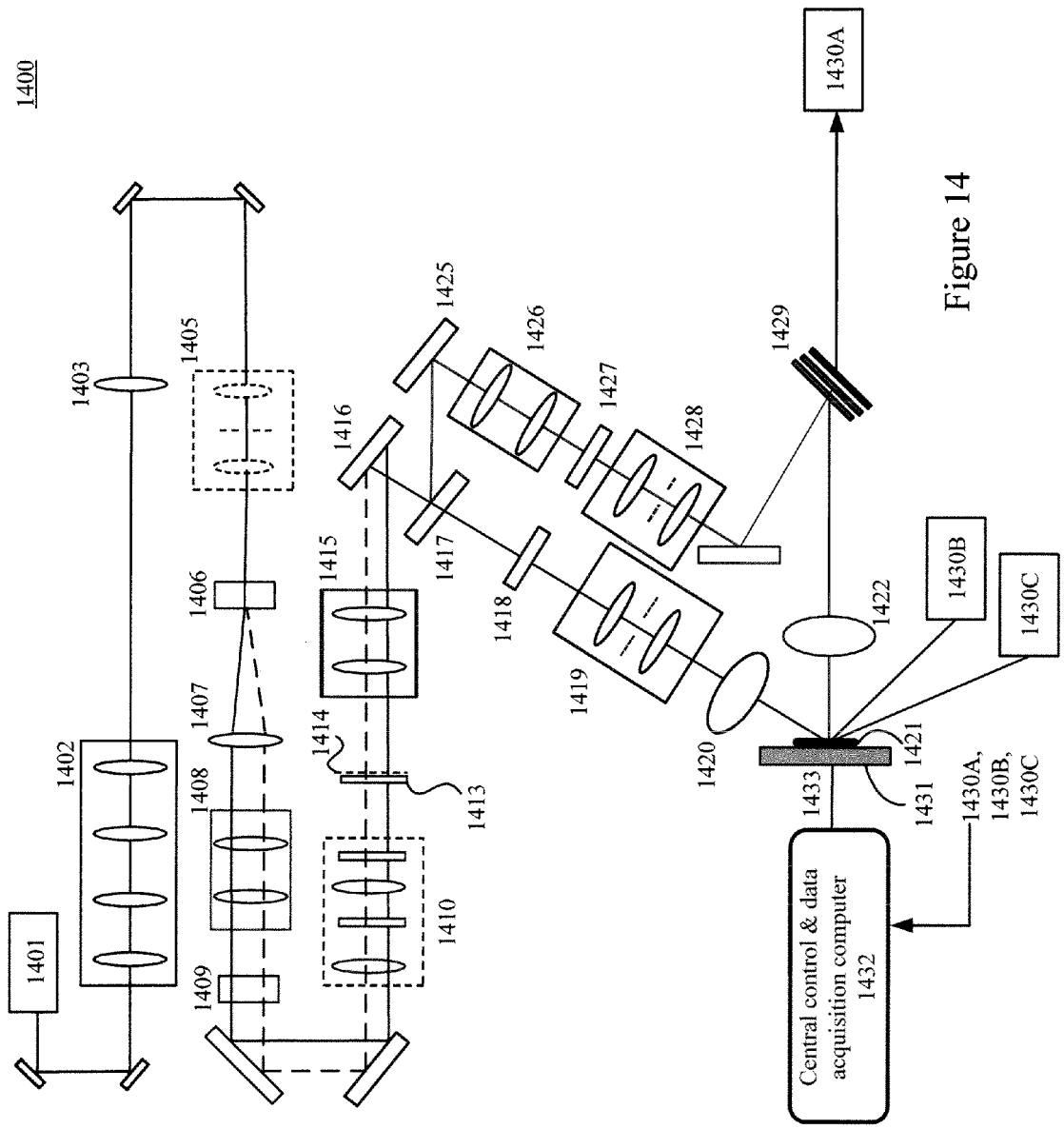
FIG. 14 illustrates an exemplary inspection system that can isolate the scattered light from multiple spots.

FIG. 14 illustrates an exemplary inspection system 1400 that can isolate the scattered light from multiple spots. Notably, system 1400 can use either normal incidence illumination or oblique incidence illumination. As known by those skilled in the art, some defects are optimally illuminated using normal incidence illumination and other defects are optimally illuminated using oblique incidence illumination. Notably, multiple collectors 1430a, 1430b, 1430c can collect the scattered light from a sample 1421, such as a wafer, using normal incidence illumination or oblique incidence illumination without reconfiguration. Specifically, as described in further detail below, no magnification change is necessary in the collectors 1430A, 1430b, and 1430c because the illumination optics are configured as described in FIG. 9C to have all spots overlap.

In inspection system 1400, light from a laser 1401 can be directed to an anamorphic waist relay (AWR) 1402. AWR 1402, which can include cylindrical lenses, prisms, gratings or spherical components (motorized or non-motorized) provides the ability to make adjusts to spot size to account for variations in laser waist parameters and system fabrication and alignment tolerances. One preferred embodiment utilizes anamorphic components that allow making adjustments to two independent axes. AWR 1402 provides its output to a collimation lens 1403.

Collimation lens 1403 provides its output to a beam shaper 1405. Beam shaper 1405 is used to adjust the size of the beam at the entrance of a prescan AOD 1406. Moreover, if laser 1401 includes a laser BBO (barium borate) doubling crystal, beam shaper 1405 can also include a slit to condition the beam as a result of the BBO crystal. This slit in beam shaper 1405 can be implemented as a standard slit, or can include one or more apodization plates or serrated slits to improve its function.

Beam shaper 1405 provides its output to prescan AOD 1406. Prescan AOD 1406 is used in deflection mode and is used in conjunction with telephoto lens 1407 and anamorphic beam expander 1408 to position and scan the beam in relation to a chirp AOD 1409. Prescan AOD 1406 scans the laser beam through an angle. A lens 1407 converts the angular scan from prescan 1406 into a linearly translation scan. Lens 1407 can be implemented as a telescope, beam expander, relay lens, focusing lens, objective lens, or any other appropriate optical component known in the art. An anamorphic beam expander 1408 is used to convert the circular output from prescan 1406 and telephoto 1407 into an oblong shape. Anamorphic beam expander 1408 can include cylindrical lenses, prisms, gratings, or spherical components. Note that the oblong-shaped beam provided by anamorphic beam expander 1408 may be necessary to accommodate limitations in the fabrication of chirp AOD 1409, specifically the height of the diffracting sound column.

Chirp AOD 1409 is used to focus the laser beam in the acoustic propagation direction and scan the laser beam. A transducer of chirp AOD 1409 can be configured to generate a signal that produces a chirp packet, which propagates over a length of chirp AOD 1409 from a start position to an end position. In one preferred embodiment, chirp AOD 1409 and prescan AOD 1406 are programmable in software to improve the system throughput, as described above in FIGS. 12A and 12B.

The output of chirp AOD 1409 can be provided to components 1410, such as a cylinder lens, a relay lens, multiple field stops/slits and polarization components. The cylinder lens is used to focus the scanning beam in the axis perpendicular to the scanning motion of chirp AOD 1409. The relay lens is used to form a real pupil at the location of downstream components 1414 and 1413 (described below). The field stops and slits are used to filter out unwanted diffraction orders from chirp AOD 1409 and pre-scan AOD 1406, as well as filter out any unwanted scattered light from other components (laser 1401 through components 1410). In addition, the slits are used as field stops to accommodate changes in the required line length. The polarization components can include components to both filter and generate a specific polarization, such as a Brewster plate polarizer, a wire grid polarizer, a prism, or any other components providing similar functionality. The polarization components can also include components to alter the polarization such as a half wave plate, quarter wave plate, or other plates providing similar functionality. These polarization components are used to provide multiple polarization options for inspecting the substrate.

Components 1410 provide their output to one or more apodization plates 1413. Apodization plate 1413 is used to change the shape of the system optical point spread function in response to the challenges provided by the sample being inspected. The apodization function can be accomplished through the use of serrated sheet metal components, dot density components, coatings, or other methods known in the art. In one embodiment, apodization plate 1413 can have independent control of the point spread function in the X and Y axes.

Apodization plate 1413 provides its output to a zero order filter slit 1414. Slit 1414 is used to remove the zero order from the optical path. Zero order slit 1414 provides its output to a magnification changer 1415. Magnification changer 1415 is used to adjust the overall illumination optics system magnification. In doing so, this changes the size of the spot, spot velocity, and the length of scan at sample 1421.

An angle of incidence mirror 1416 is an adjustable mirror used to change the angle of incidence to the wafer. When the system magnification is small and the spot size is large, the resulting numerical aperture (NA) of the pupil is small. Therefore, angle of incidence mirror 1416 can be adjusted to increase the angle of incidence (from the wafer normal) for the inspection beam. When the system magnification is large and the spot size is small, the angle of incidence mirror is positioned to decrease the angle of incidence (from the wafer normal) for the inspection beam. This adjustability provides benefits to filtering repeating structures, inspection speed, and defect signal to noise.

Angle of incidence mirror 1416 provides its output to a beam diverter 1417. Beam diverter 1417 is used to select between the oblique incidence illumination path, normal incident illumination path, or both oblique and normal incidence paths.

In the oblique incidence path, beam diverter 1417 provides its output to a DOE 1418. DOE 1418 is used to make multiple copies of the scanning beam as described previously.

DOE 1418 provides its output to an oblique fixed magnification 1419. Oblique fixed magnification 1419 is used to image the real pupil at the DOE 1418 location to the entrance pupil of an objective 1420. Objective 1420 is used to focus the beam onto the substrate being inspected.

In the normal incidence path, beam diverter 1417 provides its output to a turning mirror 1425. Turning mirror 1425 provides its output to normal incidence anamorphic beam expander 1426. Anamorphic beam expander 1426 can include cylindrical lenses, prisms, gratings or spherical components. Anamorphic beam expander 1426 is used to expand the beam in one axis or conversely reduce the beam in one axis. This expansion/reduction flexibility provides benefits to filtering repeating structures, inspection speed, and defect signal to noise.

Anamorphic beam expander 1426 provides its output to a normal incidence DOE 1427. Normal incidence DOE 1427 is used to make multiple copies of the scanning beam as described previously.

Normal incidence DOE 1427 provides its output to a normal incidence fixed magnification 1428. Normal incidence fixed magnification 1428 is used to image the real pupil at the location of DOE 1427 to the entrance pupil of an objective 1422. Objective 1422 is used to focus the spot onto the sample for the normal incidence channel.

Normal incidence fixed magnification 1428 provides its output through a turning mirror to a NI (normal incidence) beam shaper changer 1429. NI beam shaper changer 1429 serves multiple functions. It has multiple plates that serve as apertures, mirrors and beam splitters. These beam splitters can be configured to have multiple ratios for transmission and reflection (example 50/50, 100/0, 80/20, etc.). These beam splitters can also have multiple transmission and reflection profiles in a spatial sense to enable various configurations of a collection channel 1430A. Collection of scattered light is not limited to light that passes thru normal incidence objective 1422. Collection of light from the wafer can also be achieved through additional collection channels 1430B and 1430C.

Sample 1421 can be secured by a moveable platform 1431. In one embodiment, moveable platform 1431 can include a chuck, at least a linear motor (providing x-y movement), and a spindle motor (providing rotation) (optional). Moveable platform 1431 can be controlled by a central control and data acquisition computer 1432 via a motor control cable 1433.

Note that moveable platform 1431 is moving perpendicular to the direction of the scan (i.e. the sweep of the spot). In one preferred embodiment, moveable platform 1431 can be continuously moving because the scans are so much faster relative to the speed of the platform (e.g. on the order of μsecs for a scan versus seconds for the platform). Central control and data acquisition computer 1432 can receive inputs from collectors 1430A, 1430B, and 1430C.

As shown in FIGS. 15A and 15B, an angle of incidence adjuster 1501 is used in concert with the magnification changer provide multiple oblique incidence angles to substrate 1504. FIG. 15A illustrates an optional configuration for the low magnification, large spot, low NA (indicated by 1502A) configuration. In this case the adjuster 1501 is moved (shown lowered closer to objective 1503) to provide for a higher angle of incidence to substrate 1504. FIG. 15B shows the high magnification, small spot, high NA (indicated by 1502B) configuration with the adjuster 1501 in its nominal position. This position can be used for all magnification options.

As described above, the programmable chirp AOD and the DOE, which is positioned after the magnification changer, form the scans in a first direction (in this case vertical), whereas moveable platform 1431 and central control and data acquisition computer 1432 form the swaths of scans in a second direction (in this case, a horizontal direction), which is perpendicular to the first direction. The number of the scanning spots is equal to the number of swaths. An inspection system including this configuration can provide flexible spacing between adjacent, co-linear scans to eliminate spot crosstalk. Moreover, because the DOE provides spacing between the spots, inexpensive, non-imaging collectors can be used.

The various embodiments of the structures and methods of this invention that are described above are illustrative only of the principles of this invention and are not intended to limit the scope of the invention to the particular embodiments described. For example, although the embodiments are described with a predetermined number of spots, other embodiments of an illumination system or an inspection system may include a different number of spots. Thus, the invention is limited only by the following claims and their equivalents.

The invention claimed is:

1. A method of scanning a sample, the method comprising:
simultaneously forming a plurality of co-linear scans aligned along a co-linear scan line, each scan formed by a sweep of a spot by an acousto-optical device (AOD) along the co-linear scan line, the plurality of co-linear scans being separated by a predetermined spacing; and
forming a first plurality of swaths by repeating said simultaneously forming the plurality of co-linear scans in a direction perpendicular to the co-linear scan line, the first plurality of swaths having an inter-swath spacing of the predetermined spacing.

2. The method of claim 1, wherein the predetermined spacing is a scan length.

3. The method of claim 1, wherein the predetermined spacing is an integral number of scan lengths.

4. The method of claim 1, further including adjusting an AOD parameter to provide an integral number of scan lengths as the predetermined spacing.

5. The method of claim 1, further including forming a second plurality of swaths adjacent to the first plurality of swaths.

6. The method of claim 1, further including forming a second plurality of swaths adjacent to all of the first plurality of swaths except a bottom half of the first plurality of swaths.

7. The method of claim 6, wherein said forming the second plurality of swaths is performed in an opposite direction to that of the first plurality of swaths.

8. The method of claim 6, wherein said forming the second plurality of swaths is performed in a same direction to that of the first plurality of swaths.

9. An inspection system comprising:
a first acousto-optical device (AOD) configured to receive a light beam from a laser and to direct the light beam at various angles along an angular scan;
a lens configured to convert the angular scan to a linear scan;
a second AOD configured to receive the light beam in the linear scan and to generate a scan, the scan being a sweep of a spot, thereby generating a plurality of co-linear spots;
a magnification changer configured to adjust magnification of the plurality of co-linear spots, thereby generating an adjusted plurality of co-linear spots;
a first diffractive optical element (DOE) path configured to duplicate the adjusted plurality of co-linear spots such that each adjacent pair of said co-linear spots are separated by a predetermined spot spacing, thereby simultaneously generating a set of co-linear scans aligned along a co-linear scan line and having a predetermined scan spacing there between; and
a moveable platform system configured to secure a sample and forming a first plurality of swaths by moving said sample in a direction perpendicular to the co-linear scan line as the first DOE path generates a plurality of sets of the co-linear scans, said moving said sample causing said plurality of sets of the co-linear scans to form adjacent sets of the co-linear scans, the first plurality of swaths having an inter-swath spacing equal to the predetermined scan spacing,
whereby positioning the first DOE path between the magnification changer and the moveable platform system facilitates controlling the magnification changer to change a size of said plurality of co-linear spots without changing said predetermined spot spacing between each adjacent pair of said co-linear spots.

10. The inspection system of claim 9, wherein the moveable platform system is further configured to step in a direction parallel to the set of co-linear scans and, with the first DOE path, generate a second plurality of swaths, the second plurality of swaths formed adjacent to the first plurality of swaths, wherein the predetermined scan spacing is a scan length.

11. The inspection system of claim 9, wherein the moveable platform system is further configured to step in a direction parallel to the set of co-linear scans and, with the first DOE path, generate a second plurality of swaths, the second plurality of swaths formed adjacent to the first plurality of swaths, wherein the predetermined scan spacing is an integral number of scan lengths.

12. The inspection system of claim 9, wherein the moveable platform system is further configured to step in a direction parallel to the set of co-linear scans and, with the first DOE path, generate a second plurality of swaths, the second plurality of swaths formed adjacent to the first plurality of swaths, wherein the second AOD is programmable to provide an adjustable scan length for the second plurality of swaths.

13. The inspection system of claim 9, wherein the moveable platform system is further configured to step in a direction parallel to the set of co-linear scans and, with the first DOE path, generate a second plurality of swaths, the second plurality of swaths formed adjacent to the first plurality of swaths except for a bottom half of the first plurality of swaths.

14. The inspection system of claim 9, wherein the moveable platform system is further configured to step in a direction parallel to the set of co-linear scans and, with the first DOE path, generate a second plurality of swaths, the second plurality of swaths being formed in an opposite direction to that of the first plurality of swaths.

15. The inspection system of claim 9, wherein the moveable platform system is further configured to step in a direction parallel to the set of co-linear scans and, with the first DOE path, generate a second plurality of swaths, the second plurality of swaths being formed in a same direction to that of the first plurality of swaths.

16. The inspection system of claim 9, wherein the first DOE path is for either normal incidence illumination or oblique incidence illumination.

17. The inspection system of claim 9, wherein the first DOE path is for oblique incidence illumination.

18. The inspection system of claim 9, further including:
a second DOE path; and
a switching component configured to direct the adjusted plurality of co-linear spots to one of the first DOE path and the second DOE path.

19. The inspection system of claim 9, further including an anamorphic waist relay positioned to receive the light beam from the laser and configured to allow making adjustments to two independent axes.

20. The inspection system of claim 9, the laser including a barium borate laser doubling crystal, the inspection system further including a beam shaper having a slit.

21. The inspection system of claim 9, further including:
a pupil; and
one or more apodization plates placed in operative relation to the pupil and configured to provide a predetermined transmission profile to the plurality of co-linear spots.

22. The inspection system of claim 21, wherein the one or more apodization plates are configured to provide a same transmission profile in an x axis and a y axis.

23. The inspection system of claim 21, wherein the one or more apodization plates are configured to provide a different transmission profile in an x axis and a y axis.

24. The inspection system of claim 21, wherein the one or more apodization plates are configured to provide a programmable transmission profile.

25. The inspection system of claim 21, wherein the pupil is decentered with respect to objective lenses of the first DOE path.

26. The inspection system of claim 9, further including an angle of incidence mirror positioned between the magnification changer and the first DOE path, the angle of incidence mirror configured to adjust an angle of incidence to the sample.

* * * * *